US006269313B1

(12) United States Patent
Givens et al.

(10) Patent No.: US 6,269,313 B1
(45) Date of Patent: *Jul. 31, 2001

(54) METHOD FOR PREDICTING THE PRESENCE OF CONGENITAL AND THERAPEUTIC CONDITIONS FROM COAGULATION SCREENING ASSAYS

(75) Inventors: Thomas B. Givens, Rougemont; Paul Braun, Durham; Timothy J. Fischer, Raleigh, all of NC (US)

(73) Assignee: Akzo Nobel N.V. (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/517,496

(22) Filed: Mar. 2, 2000

Related U.S. Application Data

(63) Continuation of application No. 08/859,773, filed on May 21, 1997, now Pat. No. 6,101,449, which is a continuation of application No. 08/477,839, filed on Jun. 7, 1995, now Pat. No. 5,708,591.

(51) Int. Cl.⁷ .................................................... G01N 33/49
(52) U.S. Cl. .................. 702/22; 702/27; 702/28; 702/30; 702/32; 703/11; 703/12
(58) Field of Search .................. 702/19, 21, 22, 702/23, 27–32, 128, 131, 139, 179, 180, 183, FOR 131, FOR 115–FOR 119, FOR 170, FOR 171; 700/266, 268; 73/64.43; 436/66, 43, 47–50, 54, 55, 69, 174, 164, 171, 180, 805; 422/73, 50, 61–67, 68.1, 82.05; 382/133, 134, 156–159; 356/39, 40, 42; 706/924, 21, 20; 435/13; 377/10, 11; 703/6, 9, 11, 12

(56) References Cited

U.S. PATENT DOCUMENTS 3,307,392   3/1967   Owen et al. ..................... 73/64.43
3,458,287   7/1969   Gross et al. ...................... 436/69
3,658,480   4/1972   Kane et al. ....................... 436/69
4,047,890   9/1977   Eichelbenger et al. ............ 436/69

(List continued on next page.)

FOREIGN PATENT DOCUMENTS 2635081   7/1976   (DE).
3502878   1/1985   (DE).

(List continued on next page.)

OTHER PUBLICATIONS

J.W. Furlong et al., *Am. J. Clin. Pathol.*, 96:1:134–141, Jul. 1991.

J. Boone et al., *Neural Networks in Radiologic Diagnosis*, 25:9:1013–1023 (No date).

(List continued on next page.)

*Primary Examiner*—Hal Wachsman
(74) *Attorney, Agent, or Firm*—Myers Bigel Sibley & Sajovec

(57) ABSTRACT

A method and apparatus are disclosed for predicting the presence of at least one congenital or acquired imbalance or therapeutic condition associated with thrombosis/hemostasis from at least one time-dependent measurement profile. At least one time-dependent measurement on an unknown sample is performed and a respective property of said sample is measured over time so as to derive a time-dependent measurement profile. A set of a plurality of predictor variables are defined which sufficiently define the data of the time-dependent measurement profile. A model is then derived that represents the relationship between the congenital or acquired imbalance or therapeutic condition, and the set of predictor variables. Subsequently, the model is utilized to predict the existence of the congenital or acquired imbalance or therapeutic condition in the unknown sample.

35 Claims, 19 Drawing Sheets

U.S. PATENT DOCUMENTS

| | | | |
|---|---|---|---|
| 4,199,748 | 4/1980 | Bacus | 382/134 |
| 4,217,107 | 8/1980 | Yukio et al. | 436/69 |
| 4,279,616 | 7/1981 | Saito et al. | 436/69 |
| 4,289,498 | 9/1981 | Baughman et al. | 436/34 |
| 4,766,083 | 8/1988 | Miyashita et al. | 436/517 |
| 4,998,535 | 3/1991 | Selker et al. | 600/509 |
| 5,156,974 | 10/1992 | Grossman | 436/69 |
| 5,169,786 | 12/1992 | Carrol et al. | 436/69 |
| 5,388,164 | 2/1995 | Yonekawa et al. | 382/134 |
| 5,473,551 * | 12/1995 | Sato et al. | 702/19 |
| 5,473,732 | 12/1995 | Chang | 706/59 |
| 5,591,403 | 1/1997 | Gavin et al. | 426/73 |
| 5,708,591 * | 1/1998 | Givens et al. | 436/66 |
| 5,716,795 | 2/1998 | Matschiner | 435/13 |
| 5,856,114 * | 1/1999 | Mann et al. | 436/69 |
| 5,862,304 * | 1/1999 | Ravdin et al. | 706/924 |

FOREIGN PATENT DOCUMENTS

| | | |
|---|---|---|
| 115459 | 1/1983 | (EP) . |
| 434377 | 12/1989 | (EP) . |
| 525273 | 8/1991 | (EP) . |
| 841566 | 11/1996 | (EP) . |
| 2364453 | 9/1976 | (FR) . |
| 2005014 | 9/1977 | (GB) . |
| 59-203959 | 5/1983 | (JP) . |
| 60-114768 | 11/1983 | (JP) . |
| 61-272655 | 5/1985 | (JP) . |
| 5-180835 | 12/1991 | (JP) . |
| 6-027115 | 7/1992 | (JP) . |
| 6-249855 | 2/1993 | (JP) . |
| 10-104239 | 9/1996 | (JP) . |
| 2012877 | 4/1991 | (RU) . |
| 2070327 | 12/1992 | (RU) . |
| 2061953 | 3/1993 | (RU) . |
| 590665 | 11/1976 | (SU) . |
| 1076086 | 12/1982 | (SU) . |
| 1691741 | 8/1989 | (SU) . |
| 1777089 | 6/1990 | (SU) . |
| WO 8606840 | 1/1983 | (WO) . |
| WO 9101383 | 7/1989 | (WO) . |
| WO 9101497 | 7/1989 | (WO) . |
| WO 9102812 | 8/1989 | (WO) . |
| WO 9108460 | 12/1989 | (WO) . |
| WO 9116453 | 4/1990 | (WO) . |
| WO 9307491 | 10/1991 | (WO) . |
| WO 9407145 | 9/1992 | (WO) . |
| WO 9411714 | 11/1992 | (WO) . |
| WO 9416095 | 1/1993 | (WO) . |
| WO 9505590 | 8/1993 | (WO) . |
| WO 9508121 | 9/1993 | (WO) . |
| WO 9530154 | 4/1994 | (WO) . |
| WO 9614581 | 11/1994 | (WO) . |
| WO 9621740 | 1/1995 | (WO) . |
| WO 9641291 | 2/1995 | (WO) . |
| WO95 05590 | 2/1995 | (WO) . |
| WO 9642018 | 6/1995 | (WO) . |
| WO 9720066 | 11/1995 | (WO) . |
| WO 9734698 | 3/1996 | (WO) . |

OTHER PUBLICATIONS

M.A. Khanin et al., *J. Theor. Biol.*, 136:127–134 (1989).
P. Baumann et al., *Haemostasis*, 19:309–321 (1989) (No month).
C.C. Heuck et al., *Haemostasis*, 21:10–18 (1991) (No month).
J.F. Hoffman et al., "The Coag–A–Mate RA4 Fibrinogen Assay" Organon Teknika 1990, pp. 3–7, (No month).
B. Pohl et al., *Haemostasis*, 24:325–337 (1994) (No month).
A.L. Astion et al., *Arch Pathol Lab Med*, 116:995–1001 (1992), Oct. 1992.
W.R.M. Dassen et al., *Journal of Electrocardiology*, 23 (Supp.), pp. 201–202, (No date).
J.A. Swets et al., *Science*, 240:1285–1293 (Jun. 3, 1988).
D.A. Bluestein et al., *Nurse Practitioner*, 17:7:39–45 (Jul. 1991).
J.T. Brandt et al., *Arch Pathol Lab Med*, 115:109–114 (1991), Feb. 1991.
I. Talstad, *Haemostasis*, 23:19–25, 1993 (No month).
E. Baum et al., *MIT Press*, pp. 81–89, 1989 (No month).
M.L. Astion et al., *Clin. Chem.*, 39/9 pp. 1998–2004, (1993) (No month).
M.H. Zweig et al., *Clin. Chem.*, 39/4 pp. 561–577 (1993) (No month).
C.R. Schweiger et al. *Clin. Chem.*, 39/9 pp. 1966–1971 (1993) (No month).
J. Sweeney et al., Journal of the American Society of Hematology, 76:10(1) Poster #1745, Nov. 15, 1990.
J. Sweeney et al., Journal of the American Society of Hematology, 74:7(1) Poster #1509, Nov. 1989.
Sabbatini, R.M.E, "Neural Networks for Classification and Pattern Recognition of Biological Signals" *Conf. Of the Engineering in Medicine and Biology Society, U.S., New York*, IEEE, vol. Conf. 15, pp. 265–266, Oct. 28, 1993.
Pattichis C.S., et al., "Efficient Training of Neural Network Models in Classification of Electromyographic Data" *Medical and Biological Engineering and Computer*, GB, Peter Peregrinus Ltd., col. 33, No. 3, p. 499–503, May 1995.
Ortho Factor VIII:C Deficient Plasma, Ortho Diagnostic Systems, Inc. Sep. 1988, 2 pages.
American Diagnostica Inc. 3X15 Test Kit for Determination of Plasma Protein C Activity Using a Clotting End–Point, 2 pages (No date).
Package insert for Ortho Brain Thromboplastic Reagent, pp. 1–7, 1980.
The American Society of Hematology, 31st Annual Meeting Abstract Reproduction Form, 1 page (No date).
American Clinical Laboratory (Apr. 1989), 5 pages.
The Clot Signature and New Aspects in Coagulation Testing, Ortho Diagnostic Systems, Inc. (Aug. 1998), pp. 1–20.

* cited by examiner $\eta = 0.9, \alpha = 0.1$

| Hidden Layer Size | Error | | |
|---|---|---|---|
| | $E_{tr}$ | $E_{DV}$ | $\varphi_{ODB}$ |
| 2 | 0.384 | 0.376 | 0.848 |
| 4 | 0.386 | 0.354 | 0.835 |
| 6 | 0.341 | 0.328 | 0.875 |
| 8 | 0.358 | 0.327 | 0.857 |
| 10 | 0.346 | 0.325 | 0.856 |
| 12 | 0.347 | 0.322 | 0.855 |

Predictor Variables

| Predictor Variable | Description |
|---|---|
| $pv_{j1} = \left(\frac{dT}{dt}\right)_{min}$ | minimum of the first derivative |
| $pv_{j2} = t \text{ at } \left(\frac{dT}{dt}\right)_{min}$ | time index of the minimum of the first derivative |
| $pv_{j3} = \left(\frac{d^2T}{dt^2}\right)_{min}$ | minimum of the second derivative |
| $pv_{j4} = t \text{ at } \left(\frac{d^2T}{dt^2}\right)_{min}$ | index of the minimum of the second derivative |
| $pv_{j5} = \left(\frac{d^2T}{dt^2}\right)_{max}$ | maximum of the second derivative |
| $pv_{j6} = t \text{ at } \left(\frac{d^2T}{dt^2}\right)_{max}$ | index of the maximum of the second derivative |
| $pv_{j7} = T_{t_0} - T_{t_R}$ | overall change in transmittence during the reaction |

US 6,269,313 B1

METHOD FOR PREDICTING THE PRESENCE OF CONGENITAL AND THERAPEUTIC CONDITIONS FROM COAGULATION SCREENING ASSAYS

This application is a continuation of U.S. patent application Ser. No. 08/859,773 to Givens et al., filed May 21, 1997, now U.S. Pat. No. 6,101,449, which is a continuation of U.S. patent application Ser. No. 08/477,839 to Givens et al., filed Jun. 7, 1995, now U.S. Pat. No. 5,708,591, the subject matter of which is incorporated herein be reference.

This application is also related to the following publications, the subject matter of each also being incorporated herein by reference:
1. B. Pohl, C. Beringer, M. Bomhard, F. Keller, The quick machine—a mathematical model for the extrinsic activation of coagulation, *Haemostasis*, 24, 325–337 (1994).
2. J. Brandt, D. Triplett, W. Rock, E. Bovill, C. Arkin, Effect of lupus anticoagulants on the activated partial thromboplastin time, *Arch Pathol Lab Med*, 115, 109–14 (1991).
3. I. Talstad, Which coagulation factors interfere with the one-stage prothrombin time?, *Haemostasis*, 23, 19–25 (1993).
4. P. Baumann, T. Jurgensen, C. Heuck, Computerized analysis of the in vitro activation of the plasmatic clotting system, *Haemostasis*, 19, 309–321 (1989).
5. C. Heuck, P. Baumann, Kinetic analysis of the clotting system in the presence of heparin and depolymerized heparin, *Haemostasis*, 21, 10–18 (1991).
6. M. Astion and P. Wilding, The application of backpropagation neural networks to problems in pathology and laboratory medicine, *Arch Pathol Lab Med*, 116, 995–1001 (1992).
7. M. Astion, M. Wener, R. Thomas, G. Hunder, and D. Bloch, Overtraining in neural networks that interpret clinical data, *Clinical Chemistry*, 39, 1998–2004 (1993).
8. J. Furlong, M. Dupuy, and J. Heinsimer, Neural network analysis of serial cardiac enzyme data, *A.J.C.P.*, 96, 134–141 (1991).
9. W. Dassen, R. Mulleneers, J. Smeets, K. den Dulk, F. Cruz, P. Brugada, and H. Wellens, Self-learning neural networks in electrocardiography, *J. Electrocardiol*, 23, 200–202 (1990).
10. E. Baum and D. Halissler, What size net gives valid generalization? *Advances in Neural Information Processing Systems*, Morgan Kauffman Publishers, San Mateo, Calif., 81–90 (1989).
11. A. Blum, *Neural Networks in C++*, John Wiley & Sons, New York, (1992).
12. S. Haykin, *Neural Networks A Comprehensive Foundation*, Macmillan College Publishing Company, New York, (1994).
13. J. Swets, Measuring the accuracy of diagnostic systems, *Science*, 240, 1285–1293 (1988).
14. M. Zweig and G. Campbell, Receiver-operating characteristic (ROC) plots: a fundamental evaluation tool in clinical medicine, *Clinical Chemistry*, 39, 561–577 (1993).
15. D. Bluestein, L. Archer, The sensitivity, specificity and predictive value of diagnostic information: a guide for clinicians, *Nurse Practitioner*, 16, 39–45 (1991).
16. C. Schweiger, G. Soeregi, S. Spitzauer, G. Maenner, and A. Pohl, Evaluation of laboratory data by conventional statistics and by three types of neural networks, *Clinical Chemistry*, 39, 1966–1971 (1993).

BACKGROUND OF THE INVENTION

Blood clots are the end product of a complex chain reaction where proteins form an enzyme cascade acting as a biologic amplification system. This system enables relatively few molecules of initiator products to induce sequential activation of a series of inactive proteins, known as factors, culminating in the production of the fibrin clot. Mathematical models of the kinetics of the cascade's pathways have been previously proposed.

In Polh et al. (1994) supra, a dynamic model of the extrinsic coagulation cascade as described where data were collected for 20 samples using quick percent, activated partial thromboplastin time (APTT), thrombin time (TT), fibrinogen, factor(F) II, FV, FVII, FX, anti-thrombin III (ATIII), and factor degradation product (FDP) assays. These data were used as input to the model and the predictive output compared to actual recovered prothrombin time (PT) screening assay results. The model accurately predicted the PT result in only 11 of 20 cases. These coagulation cascade models demonstrate: (1) the complexity of the clot formation process, and (2) the difficulty in associating PT clot times alone with specific conditions.

Thrombosis and hemostasis testing is the in vitro study of the ability of blood to form clots and to break clots in vivo. Coagulation (hemostasis) assays began as manual methods where clot formation was observed in a test tube either by tilting the tube or removing fibrin strands by a wire loop. The goal was to determine if a patient's blood sample would clot after certain materials were added. It was later determined that the amount of time from initiation of the reaction to the point of clot formation in vitro is related to congenital disorders, acquired disorders, and therapeutic monitoring. In order to remove the inherent variability associated with the subjective endpoint determinations of manual techniques, instrumentation has been develoned to measure clot time, based on (1) electromechanical properties, (2) clot elasticity, (3) light scattering, (4) fibrin adhesion, and (5) impedance. For light scattering methods, data is gathered that represents the transmission of light through the specimen as a function of time (an optical time-dependent measurement profile).

Two assays, the PT and APTT, are widely used to screen for abnormalities in the coagulation system, although several other screening assays can be used, e.g. protein C, fibrinogen, protein S and/or thrombin time. If screening assays show an abnormal result, one or several additional tests are needed to isolate the exact source of the abnormality. The PT and APTT assays rely primarily upon measurement of time required for clot time, although some variations of the PT also use the amplitude of the change in optical signal in estimating fibrinogen concentration.

Blood coagulation is affected by administration of drugs, in addition to the vast array of internal factors and proteins that normally influence clot formation. For example, heparin is a widely-used therapeutic drug that is used to prevent thrombosis following surgery or under other conditions, or is used to combat existing thrombosis. The administration of heparin is typically monitored using the APTT assay, which gives a prolonged clot time in the presence of heparin. Clot times for PT assays are affected to a much smaller degree. Since a number of other plasma abnormalities may also cause prolonged APTT results, the ability to discriminate between these effectors from screening assay results may be clinically significant.

Using a sigmoidal curve fit to a profile, Baumann, et al [4] showed that a ratio of two coefficients was unique for a select group of blood factor deficiencies when fibrinogen was artificially maintained by addition of exogenous fibrinogen to a fixed concentration, and that same ratio also correlates heparin to FII deficiency and FXa deficiencies.

However, the requirement for artificially fixed fibrinogen makes this approach inappropriate for analysis of clinical specimens. The present invention makes it possible to predict a congenital or acquired imbalance or therapeutic condition for clinical samples from a time-dependent measurement profile without artificial manipulation of samples.

The present invention was conceived of and developed for predicting the presence of congenital or acquired imbalances or therapeutic conditions of an unknown sample based on one or more time-dependent measurement profiles, such as optical time-dependent measurement profiles, where a set of predictor variables are provided which define characteristics of profile, and where in turn a model is derived that represents the relationship between a congenital or acquired imbalance or therapeutic condition and the set of predictor variables (so as to, in turn, utilize this model to predict the existence of the congenital or acquired imbalance or therapeutic condition in the unknown sample).

SUMMARY OF THE INVENTION

The present invention is directed to a method and apparatus for predicting the presence of at least one congenital or acquired imbalance or therapeutic condition from at least one time-dependent measurement profile. The method and apparatus include a) performing at least one assay on an unknown sample and measuring a respective property over time so as to derive a time-dependent measurement profile, b) defining a set of predictor variables which sufficiently define the data of the time-dependent profile, c) deriving a model that represents the relationship between a diagnostic output and the set of predictor variables, and d) utilizing the model to predict the existence of a congenital or acquired imbalance or therapeutic condition in the unknown sample relative to the diagnostic output. In one embodiment, training data is provided by performing a plurality of assays on known samples, the model is a multilayer perceptron, the relationship between the diagnostic output and the set of predictor variables is determined by at least one algorithm, and the at least one algorithm is a back propagation learning algorithm. In a second embodiment of the present invention, the relationship between the diagnostic output and the set of predictor variables is derived by a set of statistical equations.

Also in the present invention, a plurality of time-dependent measurement profiles are derived, which time-dependent measurement profiles can be optical time-dependent measurement profiles such as ones provided by a automated analyzer for thrombosis and hemostasis, where a plurality of optical measurements are taken over time, and where the plurality of optical measurements are normalized. The optical profiles can include one or more of a PT (partial thrombin) profile, a fibrinogen profile, an APTT (activated partial thrombin time) profile, a TT (thrombin time) profile, a protein C profile, a protein S profile and a plurality of other assays associated with congenital or acquired imbalances or therapeutic conditions.

BRIEF DESCRIPTION OF THE DRAWINGS

FIG. 9 is a Table comparing hidden layer size with prediction error;

FIG. 13 is a chart listing examples of predictor variables for use in the present invention;

DESCRIPTION OF THE PREFERRED EMBODIMENTS

Figure 1:
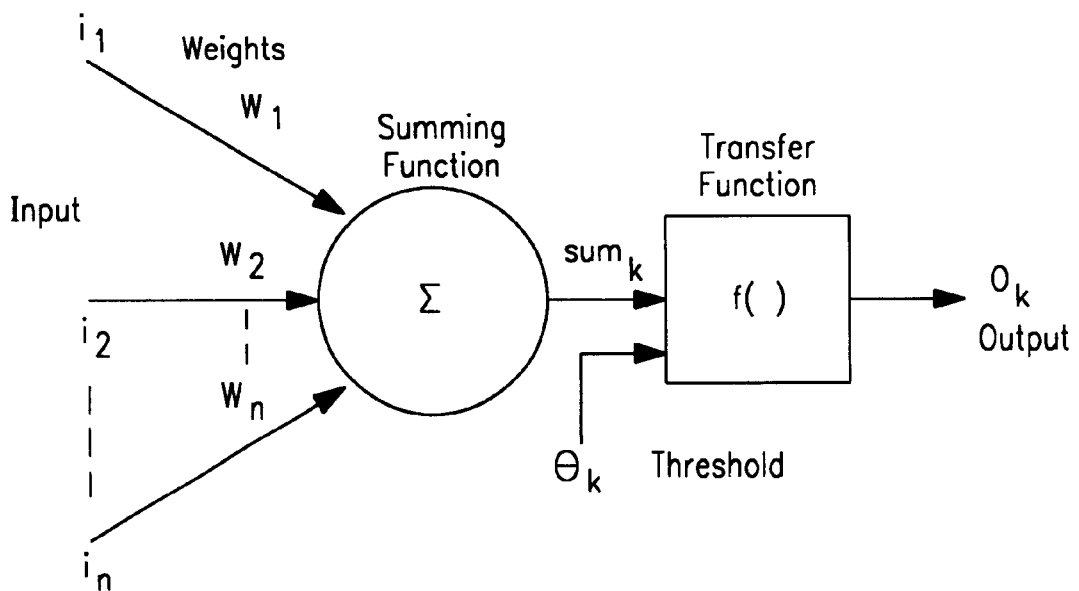
FIG. 1 is a general neuron diagram relating to the embodiment of the present invention utilizing a neural network.

In the present invention, both a method and apparatus are provided for predicting the presence of at least one congenital or acquired imbalance or therapeutic condition. As one of the first steps of the method, one or more time-dependent measurements are performed on an unknown sample. The term "time-dependent measurement" is referred to herein to include measurements derived from assays (e.g. PT, APTT, fibrinogen, protein C, protein S, TT, ATIII, plasminogen and factor assays). The terms "unknown sample" and "clinical sample" refer to a sample, such as one from a medical patient, where a congenital or acquired imbalance or therapeutic condition associated with thrombosis/hemostasis is not known (or, if suspected, has not been confirmed). In the present invention, a coagulation property is measured over time so as to derive a time-dependent measurement profile. In a preferred embodiment, the time-dependent measurement is an optical measurement for deriving an optical profile. For example, a PT profile, a fibrinogen profile, a TT profile, an APTT profile and/or variations thereof can be provided where, an unknown sample is analyzed for clot formation based on light transmittance over time through the unknown sample. In another preferred embodiment, two (or more) optical profiles are provided, such as both a PT profile and an APTT profile.

After the time-dependent measurement profiles are provided, a set of predictor variables are defined which sufficiently define the data of the time-dependent profile. One or more predictor variables comprise the set. And, in one embodiment, three or more, and in a preferred embodiment, four or more predictor variables were found to desirably make up the set. It was found that the characteristics of the time-dependent measurement profile could best be defined by one or more predictor variables, including the minimum of the first derivative of the optical profile, the time index of this minimum, the minimum of the second derivative of the optical profile, the time index of this minimum, the maximum of the second derivative, the time index of this maximum, the overall change in transmittance during the time-dependent measurement, clotting time, slope of the optical profile prior to clot formation, and slope of the optical profile after clot formation.

After defining the set of predictor variables, a model is derived which represents the relationship between a congenital or acquired imbalance or therapeutic condition and the set of predictor variables. This model can be derived from a neural network in one embodiment of the present invention. In another embodiment, the model is derived via a set of statistical equations.

Neural networks represent a branch of artificial intelligence that can be used to learn and model complex, unknown systems given some known data from which it can train. Among the features of neural networks that make them an attractive alternative for modeling complex systems are:
1. They can handle noisy data well and recognize patterns even when some of the input data are obscured or missing.
2. it is unnecessary to determine what factors are relevant a priori since the network will determine during the training phase what data are relevant, assuming there are at least some meaningful parameters in the set.

Neural networks are formed from multiple layers of interconnected neurons like that shown in FIG. 1. Each neuron has one output and receives input $i_1 \ldots i_n$ from multiple other neurons over connecting links, or synapses. Each synapse is associated with a synaptic weight, $w_j$. An adder $\Sigma$ or linear combiner sums the products of the input signals and synaptic weights $i_j*w_j$. The linear combiner output $sum_1$ and $\theta_1$ (a threshold which lowers or a bias which raises the output) are the input to the activation function $f()$. The synaptic weights are learned by adjusting their values through a learning algorithm.

After deriving the model, whether based on neural networks or statistical equations, the model is utilized to predict the existence of a congenital or acquired imbalance or therapeutic condition in the unknown sample relative to the time-dependent measurement profile(s). As such, a congenital or acquired imbalance or therapeutic condition can be predicted. Conditions which can be predicted as being abnormal in the present invention can include, among others, a) factor deficiencies, e.g. fibrinogen, Factors II, V, VII, VIII, IX, X, XI and XII, as well as ATIII, plasminogen, protein C, protein S, etc., b) therapeutic conditions, e.g. heparin, coumadin, etc., and c) conditions such as lupus anticoagulant. In one embodiment of the present invention, the method is performed on an automated analyzer. The time-dependent measurement profile, such as an optical data profile, can be provided automatically by the automated analyzer, where the unknown sample is automatically removed by an automated probe from a sample container to a test well, one or more reagents are automatically added to the test well so as to initiate the reaction within the sample. A property over time is automatically optically monitored so as to derive the optical profile. The predicted congenital or therapeutic condition can be automatically stored in a memory of an automated analyzer and/or displayed on the automated analyzer, such as on a computer monitor, or printed out on paper. As a further feature of the invention, if the predicted congenital or acquired imbalance or therapeutic condition is an abnormal condition, then one or more assays for confirming the existence of the abnormal condition are performed on the automated analyzer. In fact, in a preferred embodiment, the one or more confirming assays are automatically ordered and performed on the analyzer once the predicted condition is determined, with the results of the one or more confirming assays being stored in a memory of the automated analyzer and/or displayed on the analyzer.

EXAMPLE 1
Prediction of Heparin in Sample

This example shows a set of predictor variables that adequately describe screening assay optical profiles, develops an optimal neural network design, and determines the predictive capabilities of an abnormal condition associated with thrombosis/hemostasis (in this case for the detection of heparin) with a substantial and well-quantified test data set.

Simplastin™ L (liquid thromboplastin reagent), Platelin™ L (liquid activated partial thrombin time reagent), calcium chloride solution (0.025 M), imidazole buffer were obtained from Organon Teknika Corporation, Durham, N.C., 27712, USA. All plasma specimens were collected in 3.2% or 3.8% sodium citrate in the ratio of one part anticoagulant to nine parts whole blood. The tubes were centrifuged at 2000 g for 30 minutes and then decanted into polypropylene tubes and stored at −80° C. until evaluated. 757 specimens were prepared from 200 samples. These specimens were tested by the following specific assays: FII, FV, FVII, FVIII, FIX, FX, FXI, FXII, heparin, fibrinogen, plasminogen, protein C, and AT-III. Samples represented normal patients, a variety of deficiencies, and therapeutic conditions. Of the specimen population 216 were positive for heparin determined by a heparin concentration greater than 0.05 units/ml measured with a chromogenic assay specific for heparin. The remaining specimens, classified as heparin-negative, included normal specimens, a variety of single or multiple factor deficiencies, and patients receiving other therapeutic drugs. Positive heparin samples ranged to 0.54 units/ml.

PT and APTT screening assays were performed on each specimen utilizing two automated analyzers (MDA™ 180s) and multiple reagent and plasma vials (Organon Teknika Corporation, Durham N.C. 27712, USA) over a period of five days. When clot-based coagulation assays are performed by an automated optically-based analyzer such as the MDA 180, data are collected over time that represents the normalized level of light transmission through a sample as a clot forms (the optical profile). As the fibrin clot forms, the transmission of light is decreased. The optical profile was stored from each test.

Figure 2:
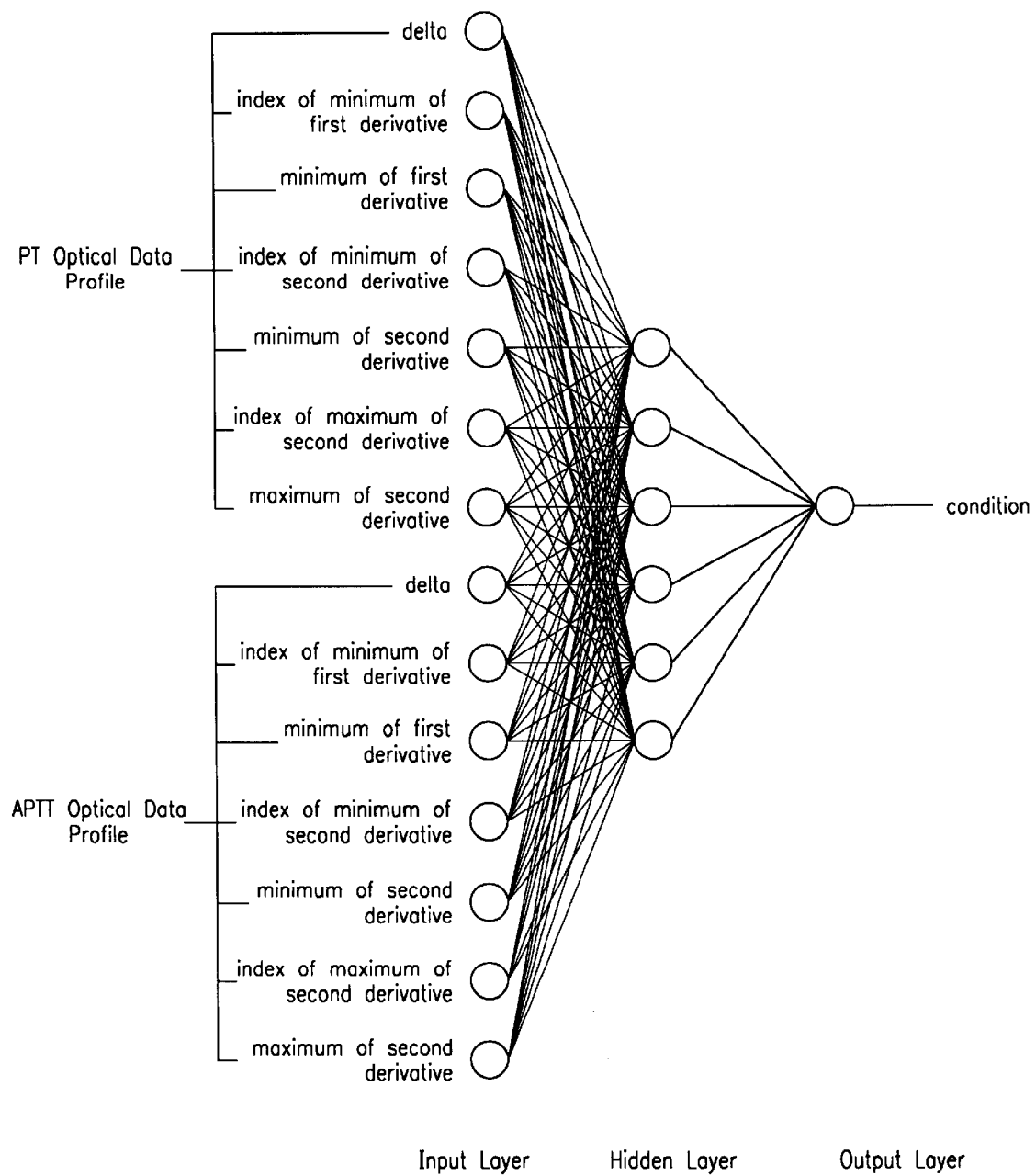
FIG. 2 is a diagram of a multilayer perceptron for predicting congenital or acquired imbalances or therapeutic conditions, relating to the neural network embodiment of the present invention.

The network configuration chosen, a multilayer perceptron (MLP) maps input predictor variables from the PT and APTT screening assays to one output variable (see FIG. 2) which represents a single specified condition A similar network was also employed for PT-only variables and APTT-only variables. This specific MLP consists of three layers: the input layer, one hidden layer, and the output layer.

Figure 3:
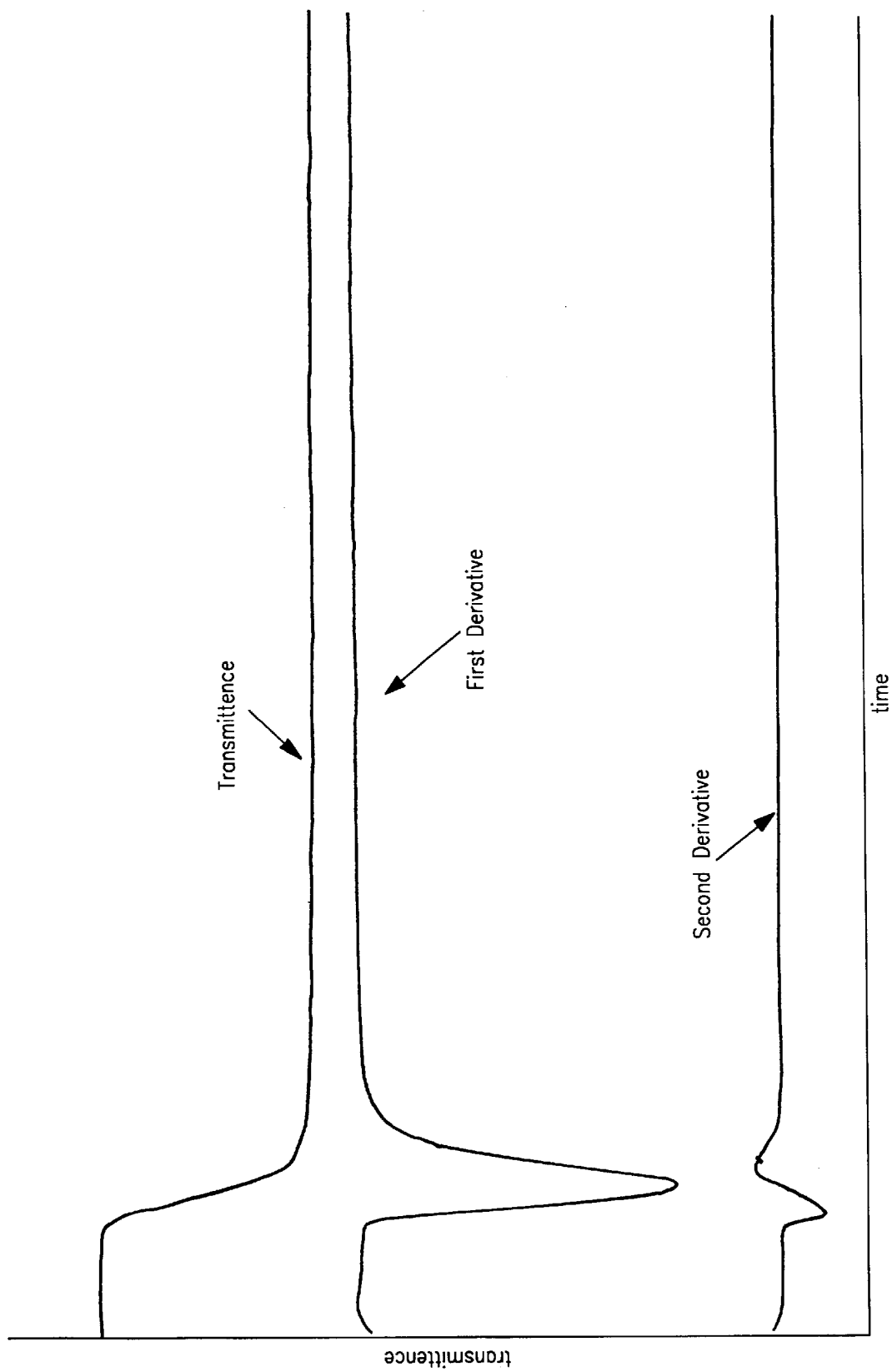
FIG. 3 is an optical profile with first and second derivatives of a normal clotting sample.

A normal optical profile is shown in FIG. 3. The set of predictor variables were chosen with the intent of describing optical profiles as completely as possible with a minimum number of variables. They are summarized in FIG. 13 where t is time from initiation of reaction, T is normalized light transmission through the reaction mixture, and pvjk is the kth predictor variable of assay j.

The predictor variables were scaled to values between 0 and 1, based on the range of values observed for each variable for assay type k $$i_j f(pv_{jk}, (pv_{j-n,k})_{min}, (pv_{j-n,k})_{max}).$$

The input variable set includes $i_{1 \ldots 7}$ for both a PT assay and APTT assay for each specimen. For known output variable values, heparin samples with results of greater than 0.05 units/ml were considered positive and assigned a value of 1 while negative samples were assigned a value of 0.

As the ratio of training set sample to the number of weights in a network decreases, the probability of generalizing decreases, reducing the confidence that the network will lead to correct classification of future samples taken from the same distribution as the training set. Thus, small samples sizes, then can lead to artificially high classification rates. This phenomenon is known as overtraining. In order to achieve a true accuracy rate of 80%, a guideline for the number of samples in the training set is approximately five times the number of weights in the network For most of this work, a 14-6-1 network was used, leading to an upward bound on the sample size of 0(450). To monitor and evaluate the performance of the network and its ability to generalize, a cross-validation set is processed at the end of each training epoch. This cross- validation set is a randomly determined subset of the known test set that is excluded from the training set.

Once the input predictor variables and output values were determined for all specimen optical profiles, the 757 sets of data were randomly distributed into two groups: 387 were used in the training set and 370 were used in the cross-validation set. These same two randomly determined sets were used throughout all the experiments.

All synaptic weights and threshold values were initialized at the beginning of each training session to small random numbers.

The error-correction learning rule is an iterative process used to update the synaptic weights by a method of gradient descent in which the network minimizes the error as pattern associations (known input-output pairs) in the training set are presented to the network. Each cycle through the training set is known as an epoch. The order or presentation of the pattern associations was the same for all epochs. The learning algorithm consists of six steps which make up the forward pass and the backward pass. In the forward pass, the hidden layer neuron activations are first determined $$h = F(iW1 + \theta_h)$$

where h is the vector of hidden-layer neurons, i the vector of input-layer neurons, W1 the weight matrix between the input and hidden layers, and F( ) the activation function. A logistic function is used as the activation function $$F(x) = \frac{1}{1 + e^{-x}}.$$

Then the output-layer neurons are computed $$o32\ F(hW2 + \theta_o)$$

where o represents the output layer, h the hidden layer and W2 the matrix of synapses connecting the hidden layer and output layers. The backward pass begins with the computation of the output-layer error $$e_o = (o - d)$$

where d is the desired output. If each element of $e_o$ is less than some predefined training error tolerance vector $TE_{tol}$, than the weights are not updated during that pass and the process continues with the next pattern association. A training error tolerance of 0.1 was used in all experiments unless otherwise specified. Otherwise, the local gradient at the output layer is then computed:

$$g_o = o(1-o)e_o.$$

Next, the hidden-layer local gradient is computed:

$$g_h = h(1-h)W2g_o.$$

Once the hidden layer error is calculated, the second layer of weights is adjusted $$W2_m = W2_{m-1} + \Delta W2$$

where $$\Delta W2 = \eta h g_o + \gamma \Delta W2_{m-1}.$$

is the learning rate, $\gamma$ is the momentum factor, and m is the learning iteration. The first layer of weights is adjusted in a similar manner $$W1_m = W1_{m-1} + \Delta W1$$

where $$\Delta W1 = \eta i e + \gamma \Delta W1_{m-1}.$$

The forward pass and backward pass are repeated for all of the pattern associations in the training set, referred to as an epoch, 1000 times . At the end of each epoch, the trained network is applied to the cross-validalion set.

Several methods were employed to measure the performance of the network's training. Error, E, for each input set was defined as $$E = \sqrt{\frac{1}{N} \sum_{q=1}^{N} (d_q - o_q)^2}.$$

The learning curve is defined as the plot of E versus epoch. The percent classification, $\phi$, describes the percent of the total test set (training and cross-validation) that is correctly classified based on some defined decision boundary, $\beta$. Receiver-Operating Characteristic (ROC) plots have also been utilized to describe trained networks' ability to discriminate between the alternative possible outcome states. In these plots, measures of sensitivity and specificity are shown for a complete range of decision boundaries. The sensitivity, or true-positive fraction is defined as $$\text{sensitivity} = \frac{\text{true positive}}{\text{true positive} + \text{false negative}}$$

and the false-positive fraction , or (1-specificity) is defined as $$(1 - \text{specificity}) = \frac{\text{false positive}}{\text{false positive} + \text{true negative}}.$$

These ROC plots represent a common tool for evaluating clinical laboratory test performance.

Using the test set described, experiments were performed to determine if the presence of heparin could he predicted with this method. First, experiments were conducted to determine optimal error-correction backpropagation learning parameters: (1) hidden layer size, (2) learning rate, and (3) momentum. Additional experiments were also conducted to compare the performance of networks based on PT and APTT assays alone with that of one combining the results of both, the effect of the training error tolerance, and the decision boundary selection.

FIG. 9 shows the effect of the hidden layer size on the training and cross validation error and the percent correct classification for the optimal decision boundary, defined as the decision boundary which yielded the lowest total number of false positives and false negatives from the total test set. As the hidden layer size is increased, the error is decreased. However, the ability to generalize does not increase after a hidden layer size of 6. The most significant benefit in terms of both error and percentage correct classification is between 4 and 6. A hidden layer size of 6 was used for the remainder of the experiments.

Figure 4:
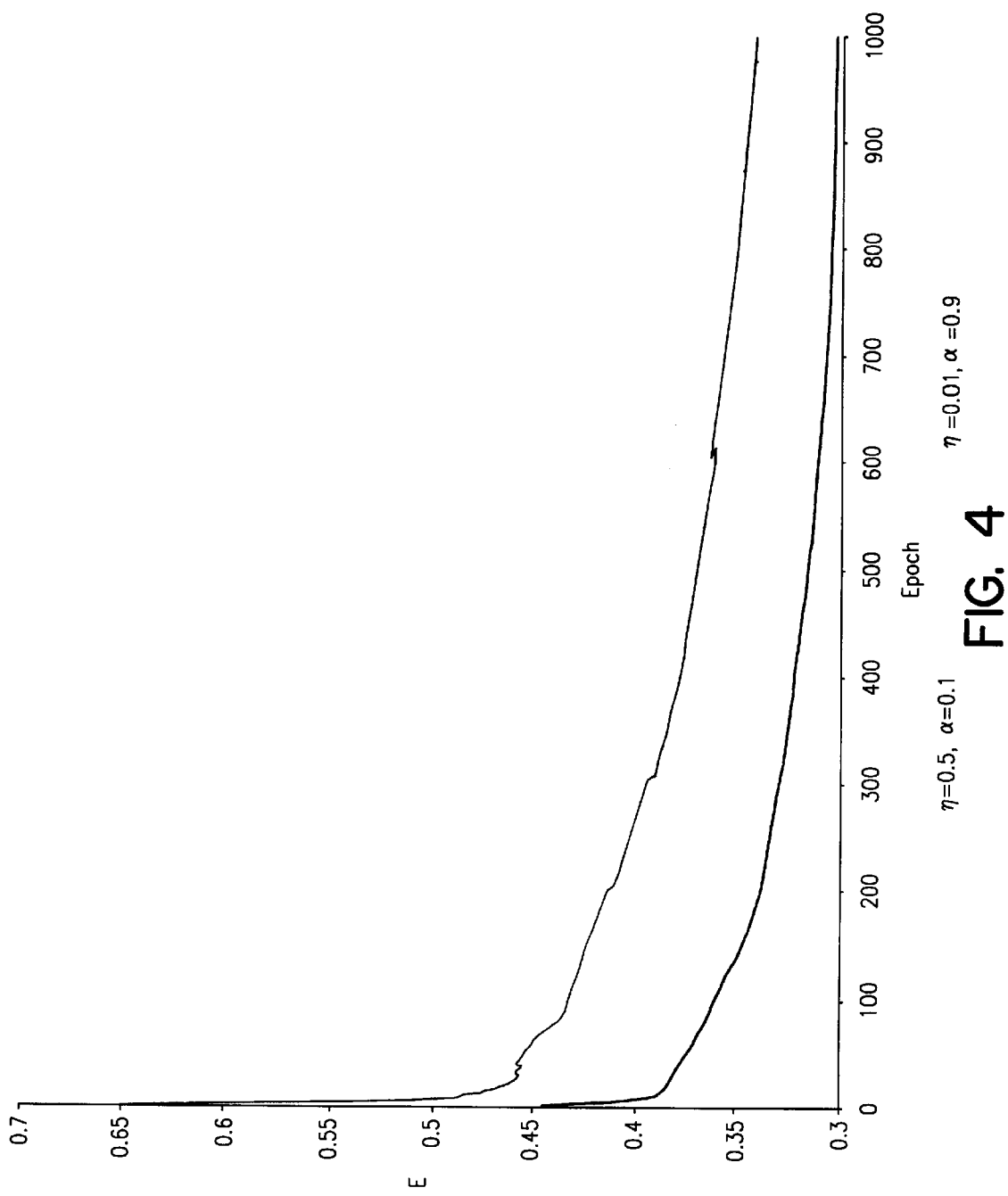
FIG. 4 is an illustration of two learning curves.
Figure 5:
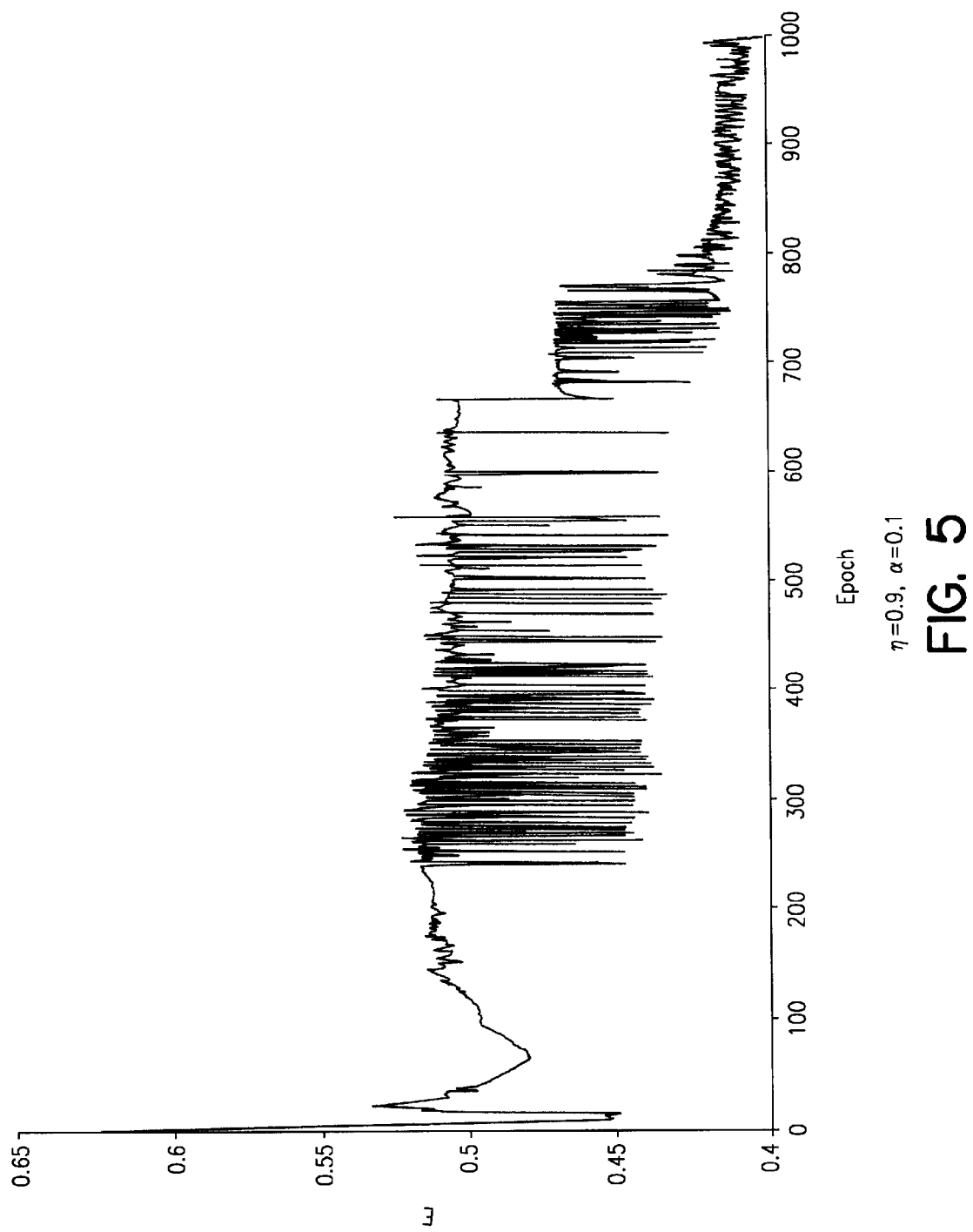
FIG. 5 is an illustration of an unstable learning curve.

A series of experiments were conducted with $\eta=\{0.01, 0.1, 0.5, 0.9\}$ and $\gamma\{0.0, 0.1, 0.5, 0.9\}$. FIG. 4 shows the learning curves for two of the best combinations of parameters. FIG. 5 shows an example learning curve when the learning rate is so high it leads to oscillations and convergence to a higher E In general, as $\eta \rightarrow 0$ the network converged to a lower E and as $\gamma \rightarrow 1$, the rate of convergence improved As $\eta \rightarrow 1$, the value of E converged too increased and oscillations increased. In addition, as $\eta \rightarrow 1$, $\gamma \rightarrow 1$ exacerbated the oscillations.

Figure 6:
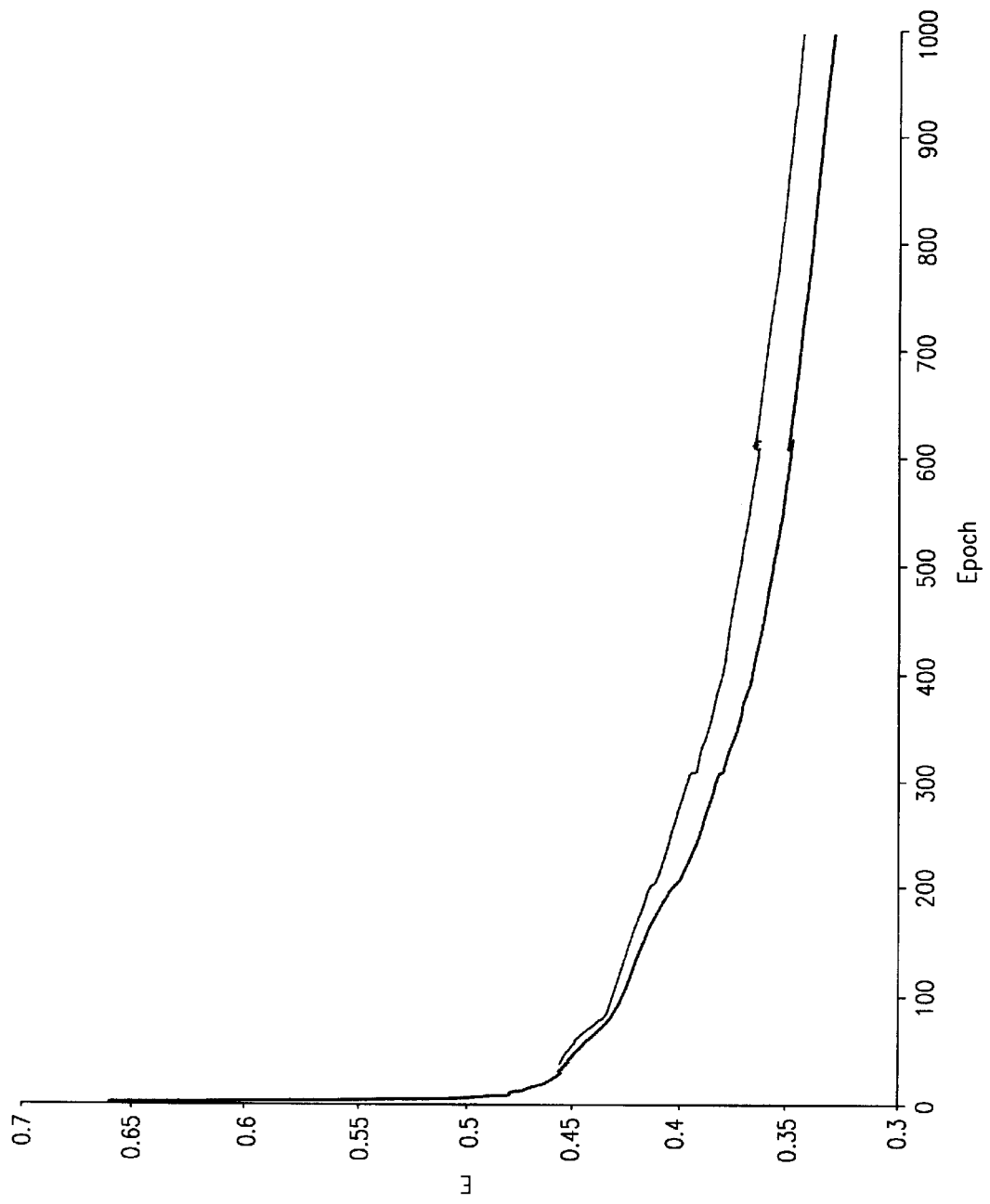
FIG. 6 is a graph showing a comparison of training and cross-validation learning curves.

FIG. 6 shows a comparison of the learning curve for the training set and cross-validation set for $\eta=0.5$ and $\gamma=0.1$. It is a primary concern when developing neural networks, and it has been previously shown that it is important to look not only at the error in the training set for each cycle, but also the cross-validation error.

Figure 7:
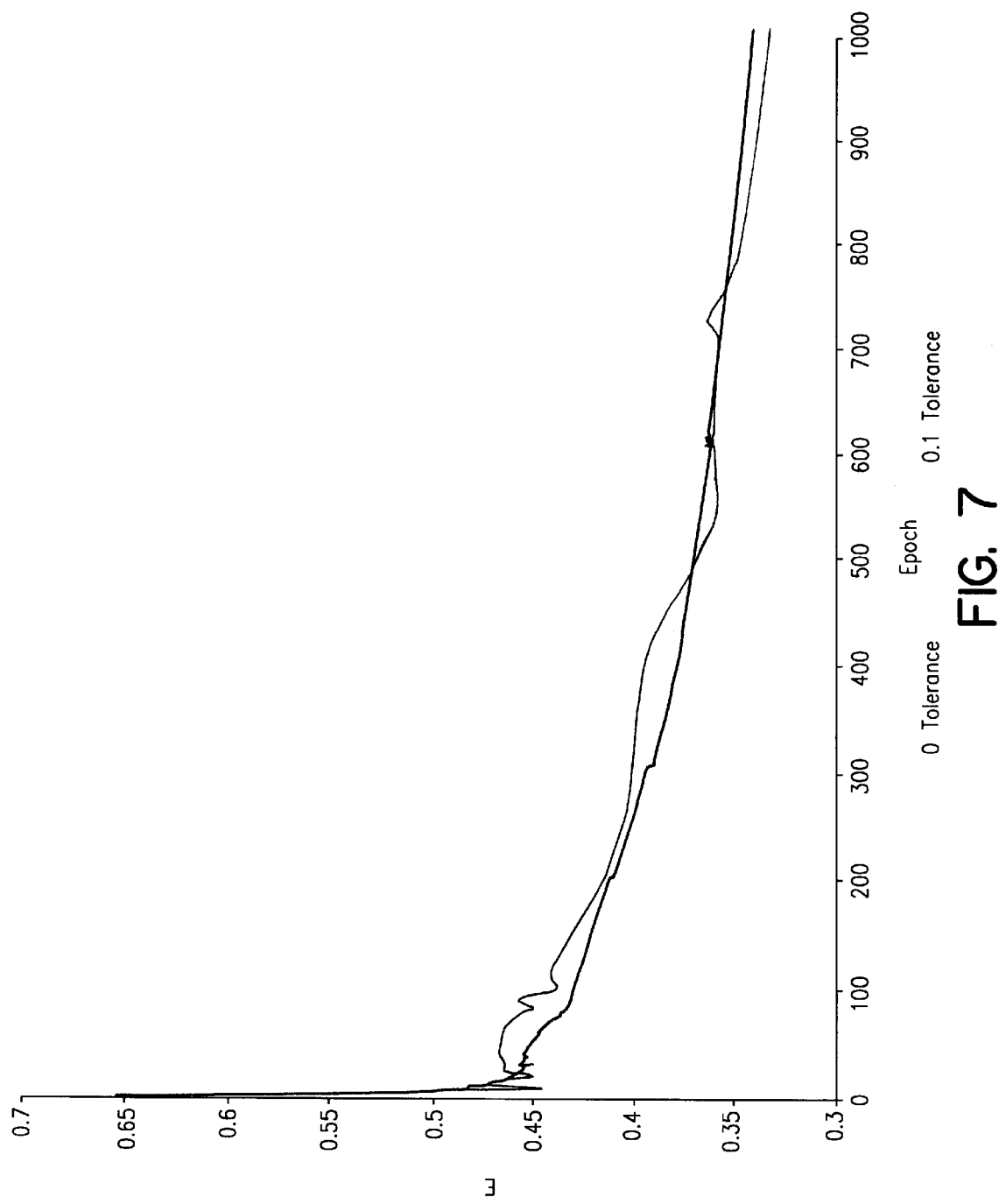
FIG. 7 is a graph showing a comparison of training error for training tolerances of 0.0 and 0.1.

FIG. 7 shows the learning curve $\eta=0.5$ and $\gamma=0.1$ and a learning tolerance of 0.0 and 0.1. These results suggest that a small learning tends to smoothen the convergence of the learning process.

Figure 8:
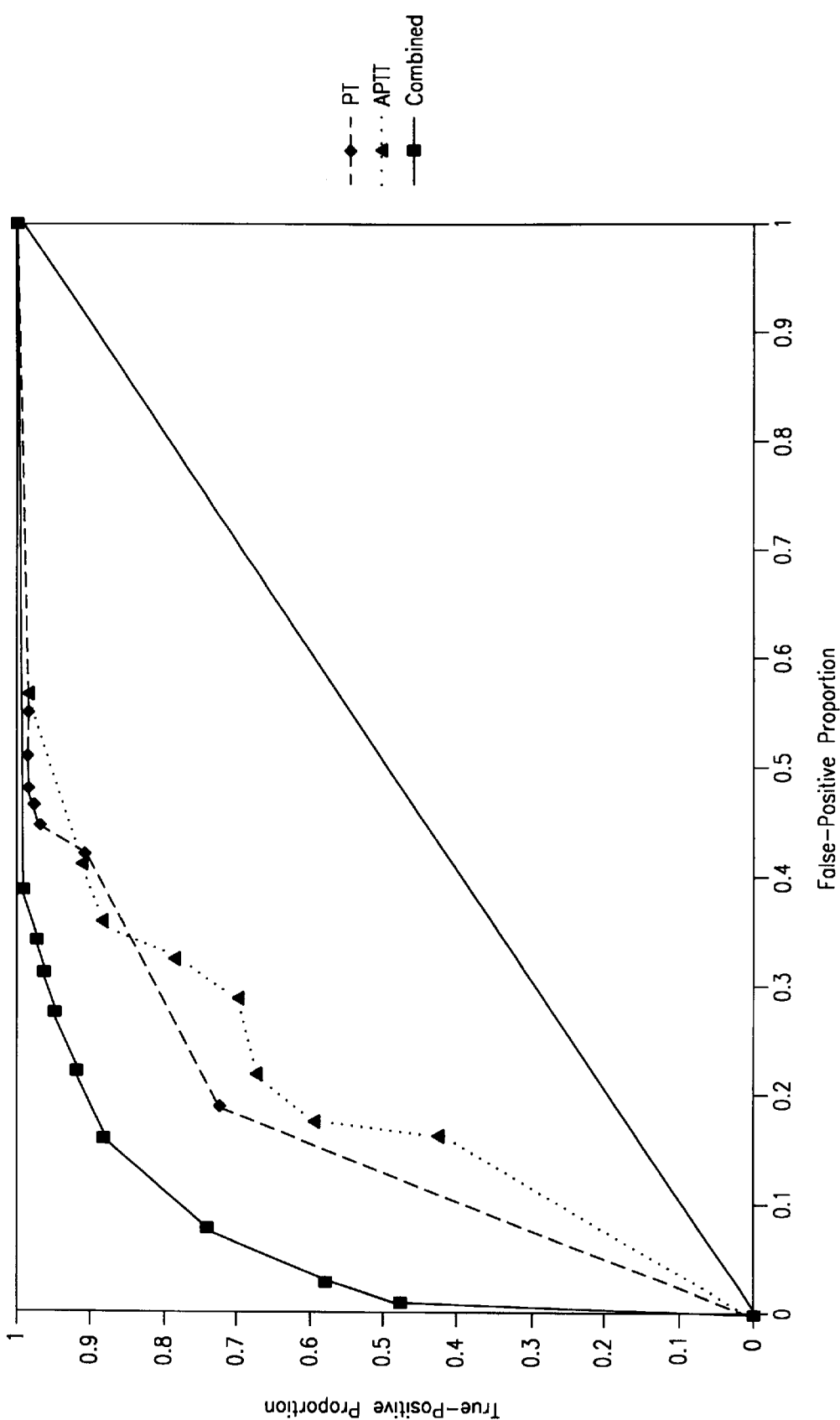
FIG. 8 is a ROC (receiver operator characteristic) illustrating the effect of decision boundary on classification.

FIG. 8 shows the ROC plot for networks trained with the predictor variables from each of the two screening assays with that of them combined. In the single assay cases, the hidden layer size was 3. While using the data from one assay does lead to some success, using the information from both assays makes a significant improvement in the ability of the network to correctly predict the presence of heparin This graph indicates that a 90%. true positive proportion can be achieved with a false positive proportion of 15%. Using a single assay, a 60–70% true positive proportion can be achieved with a false positive proportion of approximately 15%.

EXAMPLE 2

Factor VIII

Figure 10:
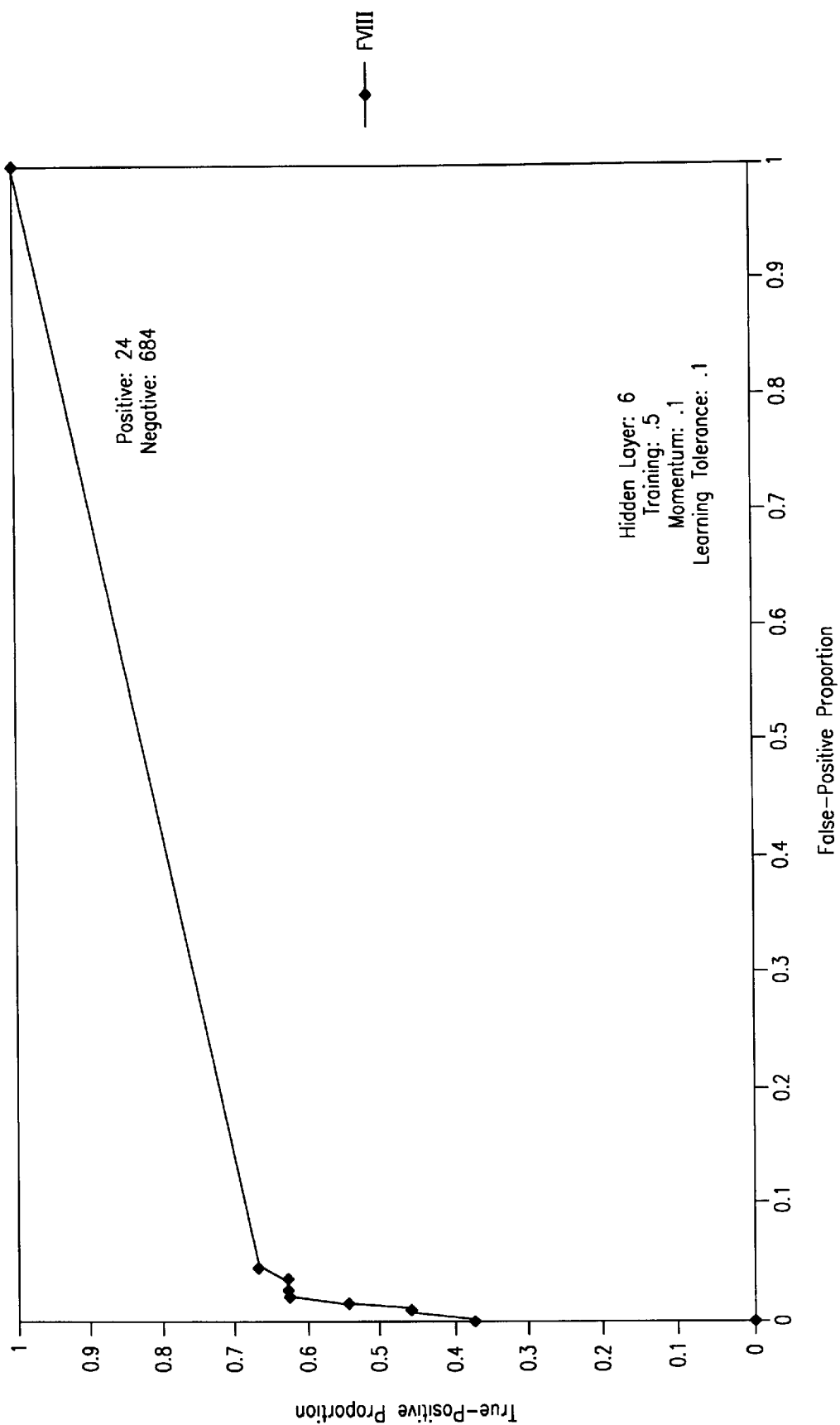
FIG. 10 is a receiver operator characteristic plot related to predicting an abnormality in relation to Factor VIII.
Figure 11:
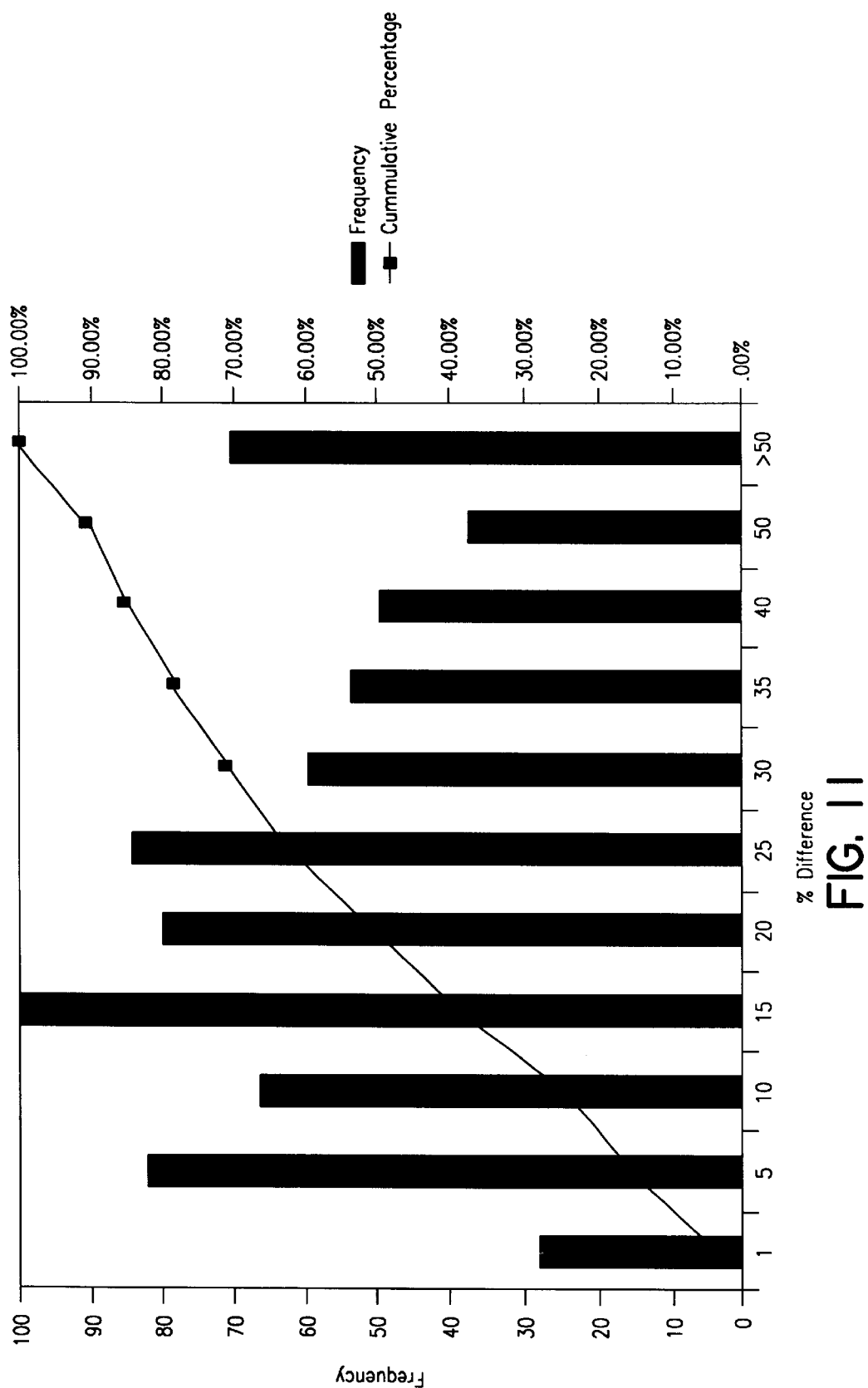
FIG. 11 is a graph demonstrating the ability to predict actual Factor VIII activity.

Similar tests were run as in Example 1. As can be seen in FIGS. 10 and 11, two training sessions were conducted for predicting a Factor VIII condition in an unknown sample. FIG. 10 is a receiver operator characteristic plot related to predicting an abnormality in relation to Factor VIII. In FIG. 10, everything below 30% activity was indicated as positive, and everything above 30% was indicated as negative. Cutoff values other than 30% could also be used. In this Example, the activity percentage has a known accuracy of approximately + or –10%. In FIG. 11, the actual percent activity was utilized as the output.

EXAMPLE 3

Factor X

Figure 12:
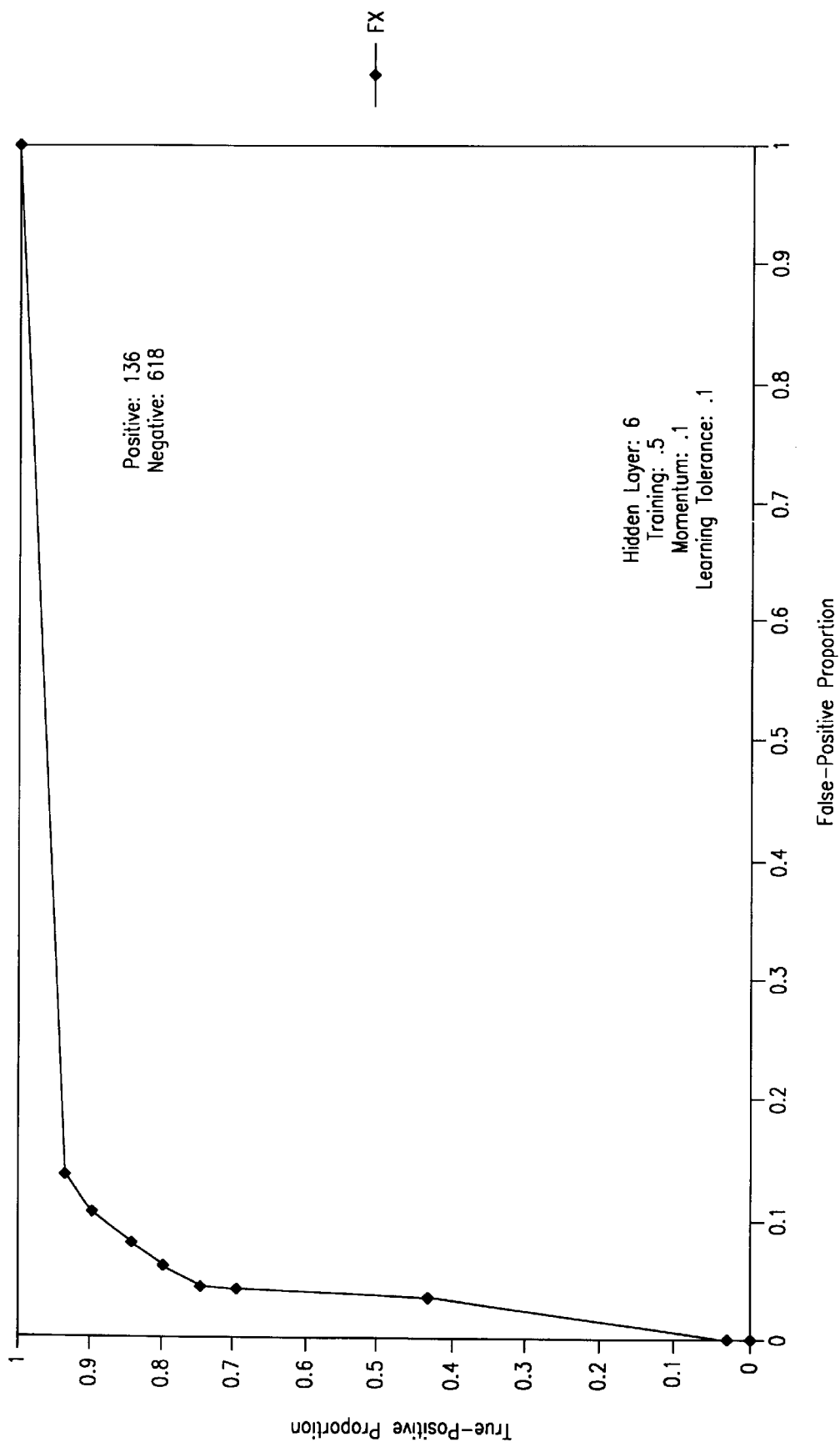
FIG. 12 is a receiver operator characteristic plot related to predicting an abnormality in relation to Factor X.
Figure 14:
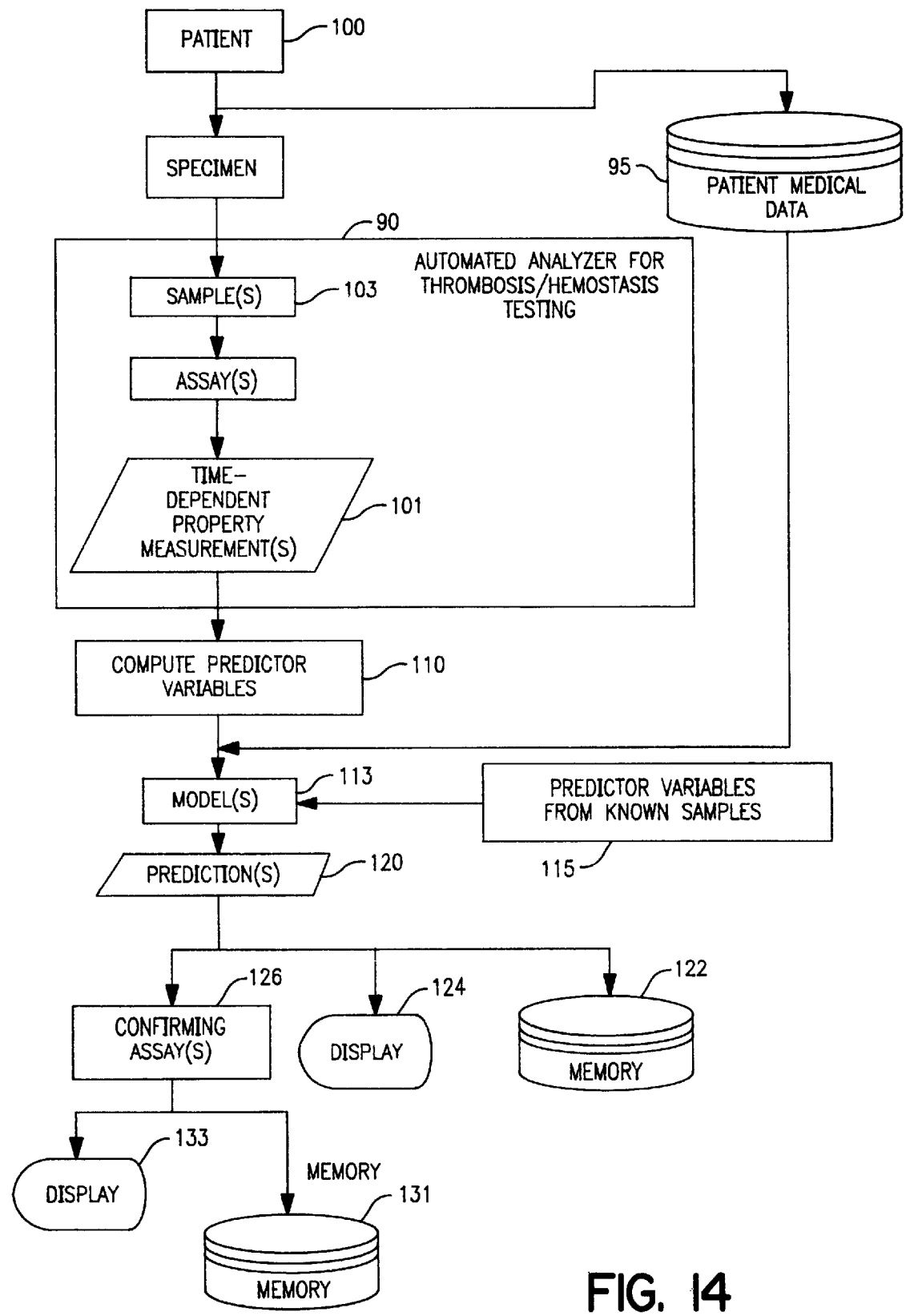
FIG. 14 is a chart illustrating key aspects of the present invention.

As can be seen in FIG. 12, the method of the present invention was run similar to that as in Example 2, where here an abnormality in Factor X concentration was predicted from unknown samples. Everything below 30% activity was indicated as positive, and everything above 30% was indicated as negative Cutoff values other than 30% could also be used.

The results of the cross-validation sample sets throughout the experiments indicate that the sample size was sufficient for the network to generalize. While the random distribution of the training and cross-validation sets were held constant throughout the experiments presented, other distributions have been used. These distributions, while all yielding different results, still lead to the same general conclusion.

Many alternatives for or additions to the set of predictor variables were explored. This included coefficients of a curve fitted to the data profile, pattern recognition, and clot time- based parameters. Low order functions tend to lose information due to their poor fit, and high order functions tend to lose information in their multiple close solutions. Clot-based parameters, such as clot time, slope in the section prior to the initiation of clot formation, and afterwards, are often available, but not always (because in some samples, the clot time is not detectable). The successful results observed indicate that the set of predictor variables used are effective for predicting congenital or acquired imbalances or therapeutic conditions.

The optimization of the network learning algorithm's parameters made significant differences in its performance In general, performance was best with low learning rates, high momentum rates, some small training error tolerance, and a hidden layer size approximately half of the size of the input layer Overview of the Automated Analyzer The automated analyzer is depicted in FIGS. 15–20, the numbered components of which are described in U.S. Pat. No. 5,646,046, which has been incorporated by reference.

The analyzer is fully automated in terms of specimen handling, sample preparation, optical inspection, signal processing and total quality control for imprecision and bias, and a quality assurance program.

A. The Specimen Handling Segment.

The specimen handling segment of the analyzer is divided into four basic components consisting of positive patient identification of the sample, screening for preanalytical variables, the ability to do closed container sampling and the ability to continuously supply cuvette wells for sample evaluation.

In greater detail, the specimen handling segment consists of:

1) a means for storing and continuously supplying a plurality of cuvettes to be used in the assays, each cuvette containing a plurality of reaction wells;

2) the optically readable code, such as a bar code or other coding, present on or incorporated into the sample collection tube or holding device containing a sample of serum, plasma or whole blood, is a patient identification and tracking device, and is also used in assay entry and automatic tracking of the assay during sample evaluation;

3) a means for the screening of and evaluating preanalytical variables prior to the beginning of any assay, such as hemolysis, bilirubin and lipemia; and 4) a sample insertion station including a means for automatically aspirating sample from the sample collection tube or holding device with or without a stopper and for automatically dispensing the aspirated sample into a reaction well of a cuvette.

B. The Sample Preparation Segment.

The sample preparation segment of the analyzer consists of four components: the means for defining unique reagent transferring sequences for each assay, random access ability, or the ability for a probe to aspirate reagent from a reagent container and dispense it into a predetermined cuvette well in any order and to aspirate and deliver different plasmas without cross contamination; the universal profile testing method; a means for performing auto dilutions of the sample; and a means for monitoring reagents and samples.

In greater detail, the sample preparation segment consists of:

1) an assay definition file ("adf") that allows for flexibility in how the reagents and plasmas are delivered. This flexibility is defined in terms of aspiration and dispense velocities, temperature, time out (delay) or timing sequences;

2) a reagent station, including a sample preparation means having the ability to randomly aspirate selected amounts of selected reagents from selected reagent containers as needed, and for dispensing the aspirated reagents into a reaction well of a cuvette according to the directions given in a programmed test for the sample in that reaction well. Each well of the cuvette may be programmed to have a different assay performed, and the reagent and sample in the reaction well forms a reaction volume which exhibits optical characteristics to be monitored by the analyzer;

3) a means for providing a universal temperature profile for the different assays programmed on the analyzer, which is an arrangement for temperature regulation of a fluid sample in a cuvette transported through various stations of the automated system for optically monitoring the sample in the cuvette, comprising: a means for transporting the cuvette through the various stations of the sample and reagent delivery system and optical monitoring system, the sample temperature being controlled by the system; cooling means for cooling the sample in the first portion of the profile; heating means for heating the sample in the third portion of the profile in such a way as to maintain the sample temperature within base tolerance constraints; and a second section providing a means of providing a temperature ramp that defines the sample transition from the initial cool temperature to final warm temperature;

4) a means for automatically diluting samples, reference materials, and control materials through the use of programmed probes that perform a wide range of serial and nonserial dilutions; and 5) a temperature controlled housing for storing a plurality of reagent containers, each containing a respective reagent, and a plurality of sample collection tubes, each containing a fluid sample and presenting an optically readable code, such as a bar code or other equivalent coding, identifying the sample and a test to be performed on the sample. There is also a reagent tracking system that monitors the amount of available fluid in each discrete vial or container of reagent, present as a means for sensing liquid levels, one embodiment being a liquid-level sensor on each probe that aspirates and dispenses liquid.

C. The Optical Inspection Segment.

The optical inspection segment of the automated analyzer consists of three components, 1) a means for multiple wavelength analysis; 2) the use of a broad spectrum of wavelengths; and 3) continuous normalization of the fluctuations in light levels associated with sample to sample variability.

The optical inspection portion of the analyzer is provided for by:

1) a multichannel optical monitoring system as described in commonly owned U.S. Pat. No. 5,002,392, issued on Mar. 26, 1991, and commonly owned U.S. Pat. No. 5,245,176, "Method for Scanning Photodiodes"; and 2) fluctuations in light levels associated with sample to sample variability, such as differences in color from sample to sample, are normalized through a quality assurance program prior to data analysis of the test results.

D. The Signal Processing Segment.

The signal processing segment of the analyzer can include: the determination of kinetic endpoints; complex processing that determines endpoints other than clot formation, such as immunological complexes or chromogenic endpoints; and an on-line database against which each test result can be compared. The signal processing segment also includes the analysis of the clot waveform as set forth in detail herein above.

E. The Quality Assurance Segment.

The satisfactory performance of any and all clinical laboratory assays depends on an effective quality control or quality assurance program, which controls each of the parameters listed below. Control of these parameters minimizes imprecision associated with random error and minimizes bias associated with systemic error. The parameters controlled by the analyzer are:

A) specimen integrity and handling;

B) reagent and expendable availability and quality;

C) suitability and sensitivity of mechanical metering devices;

D) suitability and sensitivity of reaction inspection and measuring devices;

E) suitability and sensitivity of data analysis methods, wherein statistical quality control rule analysis of the control data allows for the monitoring of the system in statistical control, assuring the validity of the results; and F) minimized bias when compared to reference methods.

In order to assure accurate laboratory assay results, it has always been necessary to devise quality assurance methods to monitor important variables of each of the above critical parameters. This type of monitoring is equally necessary for manual, semi-automated and automated analytical methods. Prior to the present invention, skilled laboratory workers were responsible for monitoring these important variables for manual and semi-automated analytical methods using rudimentary off-line means. Some of these means included a traditional Levy Jennings approach to control ruling, visual inspection of samples for anomalies and no real-time monitoring of some instrument parameters was available.

Although each type of coagulation laboratory assay has specific critical parameters within the general parameters described above, some additional hemostasis and thrombosis assay critical parameters include:

1) Positive patient identification which includes bar code or similar identifier tracking, Delta check with previous specimen from the same patient; physiologic panic value evaluation; operational comments regarding the sample that follow data to the final report; and a statistical evaluation of replicate tests.

2) Preanalytical Variables are variables that can contribute to an anomalous result. Examples are specimen age, plasma with clot contamination, the amount of anticoagulant present in the blood collection tube to plasma collected ratio, nonanalyte interferences, optimized thermal storage of specimens to offset degradation with activation, hemolysis of sample, bilirubin content, and lipemic samples.

3) Sampling from a primary specimen container that allows for repeated testing from the same closed container without plasma carryover effects or aerosolization of the blood samples.

4) Reagent and Expendable Availability—a broad diagnostic assay menu supported with the proper reagents, which are monitored, tracked and flagged for the operator when the levels are low; a liquid level sensor on the probe via, for example, capacitance touch facilities; flagging failure of the analyzer to dispense; logic programming omitting the performance of an assay if sufficient reagents not available; bar code or similar identifier identification of the actual placement of a reagent in reagent tray; and preloaded cuvette cassettes handling a large number of cuvettes insure the optical clarity of the cuvette by minimizing handling of cuvettes.

5) Reagent quality is insured by refrigerated storage; by a reagent tray cover that minimizes evaporation and condensation; by the tracking of expiration dates; by tracking of reagent quality within each run, day-to-day, and month-to-month via an on-board quality control program using controls; by an assay specific quality control program which employs statistical rules with the ability to detect errors in the reagents; by tracking reagent quality independently of biological control plasmas using averaged patient data parameters; by normalizing minor drifts in reagent viability over time by assay calibration using calibrator plasmas; and by stirring reagents requiring stirring to maintain homogeneous suspension.

As can be seen from the above descriptions of the various segments of the automated coagulation analyzer, the segments are interdependent. Each of the four segments, specimen handling, sample preparation, optical inspection and signal processing are monitored and regulated and checked by on-board quality assurance and quality control program, providing an oversight function for all critical parameters. Each of these segments will be now more fully discussed along with the integration of these segments with the quality control and quality assurance features of the automated coagulation analyzer.

I. Specimen Handling

The analyzer automatically handles the sample to be tested from the moment the collection tube containing the sample is placed in the analyzer. The analyzer has a first transporting device for transporting the sample collection tubes, in order, first to the programming station and then to the sample insertion station and a second transporting device for transporting the cuvettes through the sample insertion station, the reagent station and on to the optical monitoring device where the optical characteristics of the reaction volume in the respective reaction wells can be monitored.

The sample collection tubes can be evacuated and sealed by a septum, the tubes are sampled with a piercing/aspirating sample probe which deposits the proper amount of sample into the well of a cuvette. The preferred cuvette is described in Karp et al. U.S. Pat No. Des. 325,090 and U.S. Pat. No. 5,040,894.

According to another aspect of the invention, the temperature controlled housing maintains the temperature of the evacuated collection tubes and the reagent containers between 9° C. and 100° C.

Further, the second transporting device preferably includes a linear track for guiding the cuvettes and a drive mechanism for periodically moving the cuvettes along the track in discrete increments. Preferably, the drive mechanism includes a lead screw and the cuvettes are each shaped for engaging the lead screw for being driven along the linear track in the manner described in the above referenced U.S. Pat. No. 5,040,894. According to yet a further aspect of the analyzer, the cuvette storage includes a device for removing the cuvettes from the storage and placing the cuvettes onto the linear track.

Additionally, the first transporting device preferably includes a plurality of shuttles each for holding a plurality of sample collection tubes and means for moving the shuttles through the programming and sample insertion stations.

Each sample is given a machine-readable identification, such as a bar code, which is used in assay entry and during tracking of the assay. For example, a freshly drawn tube of blood is manually labelled with a bar code, and the bar code, patient identification and required tests are manually entered into the analyzer's computer. The tube is then placed into a shuttle and the shuttle placed in the shuttle storage area, where its bar code is automatically read by the analyzer and tracked by the quality control programming. The septum is pierced with the sampling probe, called Probe 1, which has been programmed as defined in the adf, to withdraw a specified amount of sample from the tube or collection device, which proceeds to aspirate the sample and dispense it into a predetermined well of a predetermined cuvette. The probe is then washed in order to remove essentially all of the sample remaining on it, in order to avoid cross-contaminating the next sample. Wash solutions include, among others, water, bleach solutions, preferably a 10% bleach solution, or specifically formulated wash solutions that are capable of removing essentially all of the sample from the probe. At times later in the assay, each probe can be washed after each use, for the same reasons. However, another reason for washing a probe is because in these types of assays, should thrombin, thromboplastin or phospholipids contaminate the probe, they are extremely difficult to remove, and thereby contaminate the next assay well. Removal of these extremely sticky substances from the probe is needed for both the method and the instrument to perform.

The analyzer has been programmed so that this particular well will have a specific assay performed in it. The quality assurance program tracks the well at specified times throughout the test procedure, confirming assay identification, correct volume delivery, correct adf interpretation and proper temperature control at critical times.

Preanalytical variables, such as the presence of hemolysis, bilirubin, lipemia, and fibrin clots are determined in conjunction with the performance of an assay. This is accomplished by utilizing a bichromatic technique inspecting a baseline wavelength and wavelength where the substance of interest can be detected. Unique algorithms are then applied to quantitate each substance. For example, hemolysis is detected by monitoring transmittance at 535 nm and 515 nm and computing a hemolysis index, which is $$\text{Hemolysis Index } (HI) = \frac{\text{Normalized transmittance at 535 nm}}{\text{Normalized transmittance at 515 nm}}$$

Figure 15:
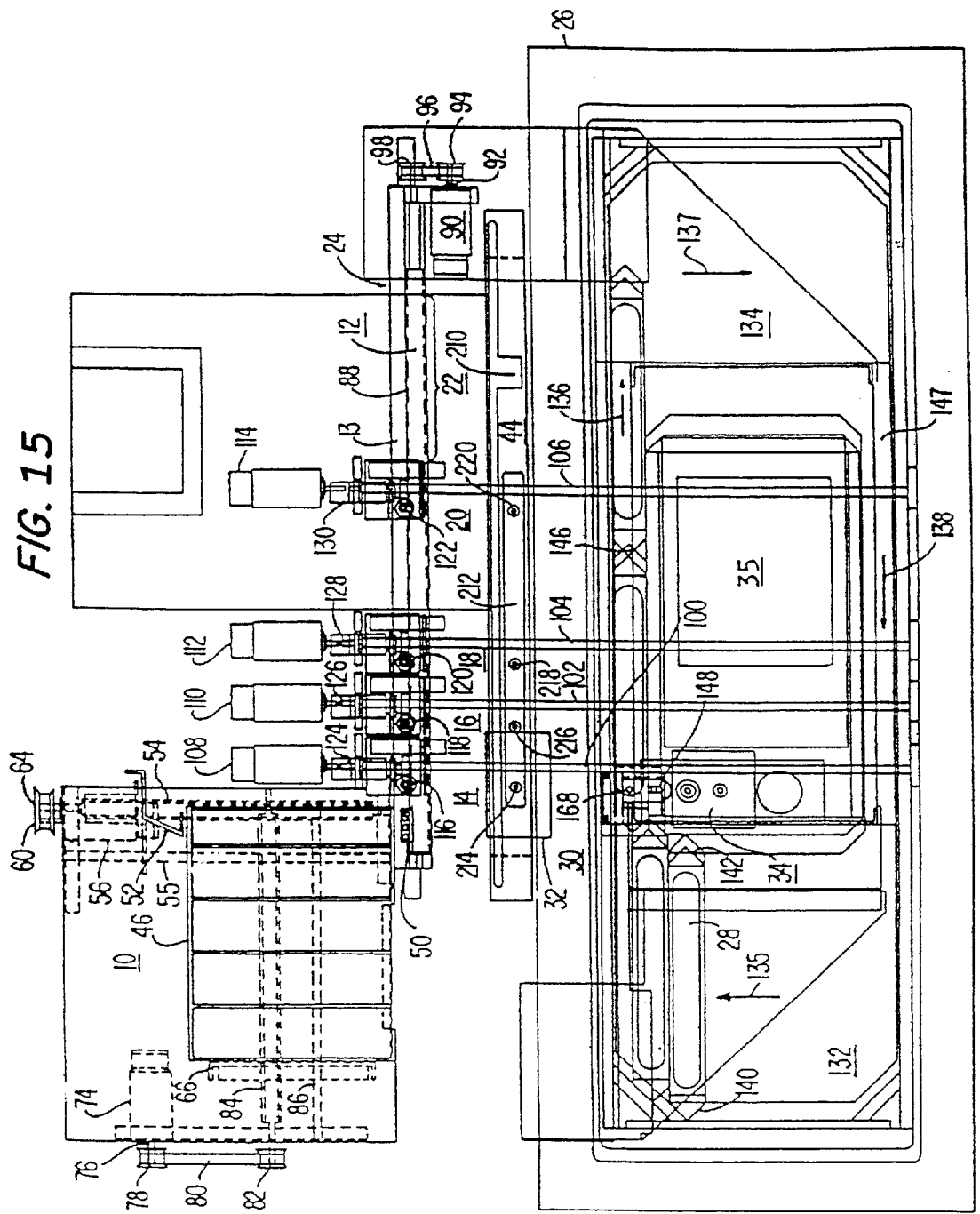
FIG. 15 is a schematic top elevation of a sample handling system in an optical evaluation instrument according to the invention.
Figure 16:
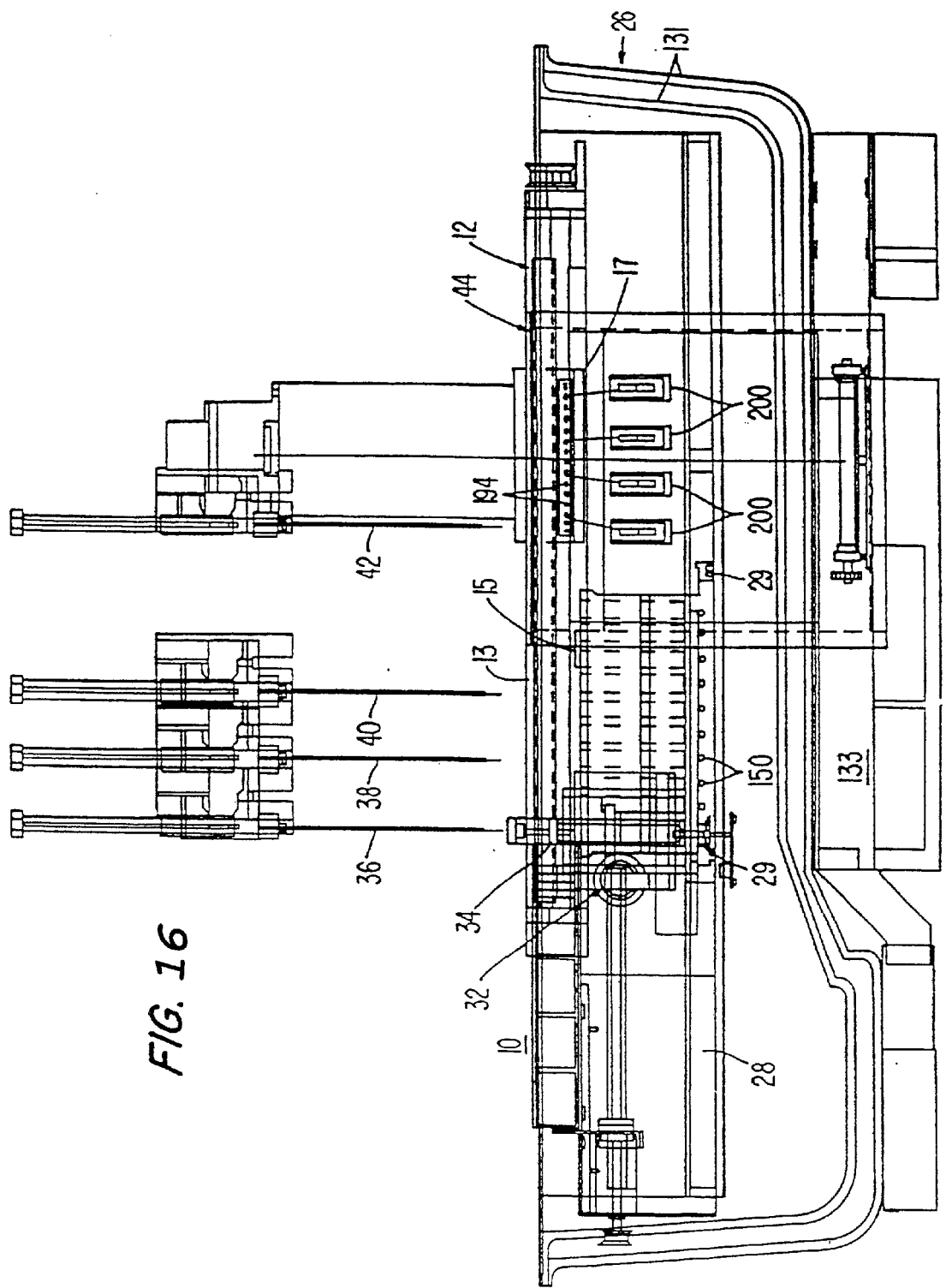
FIG. 16 is a schematic front elevation of FIG. 15.
Figure 17:
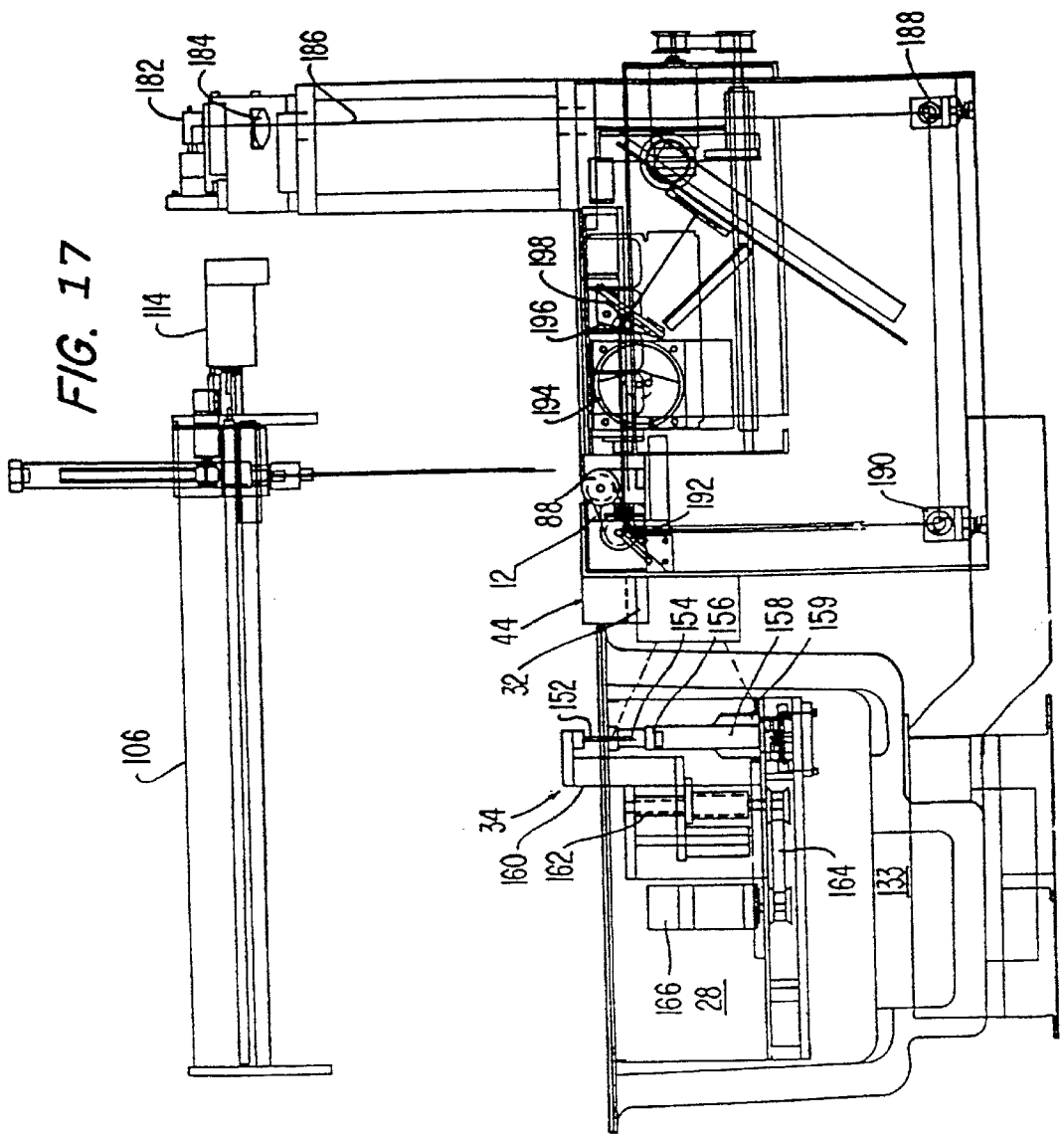
FIG. 17 is a schematic right-side elevation of FIG. 15.
Figure 18:
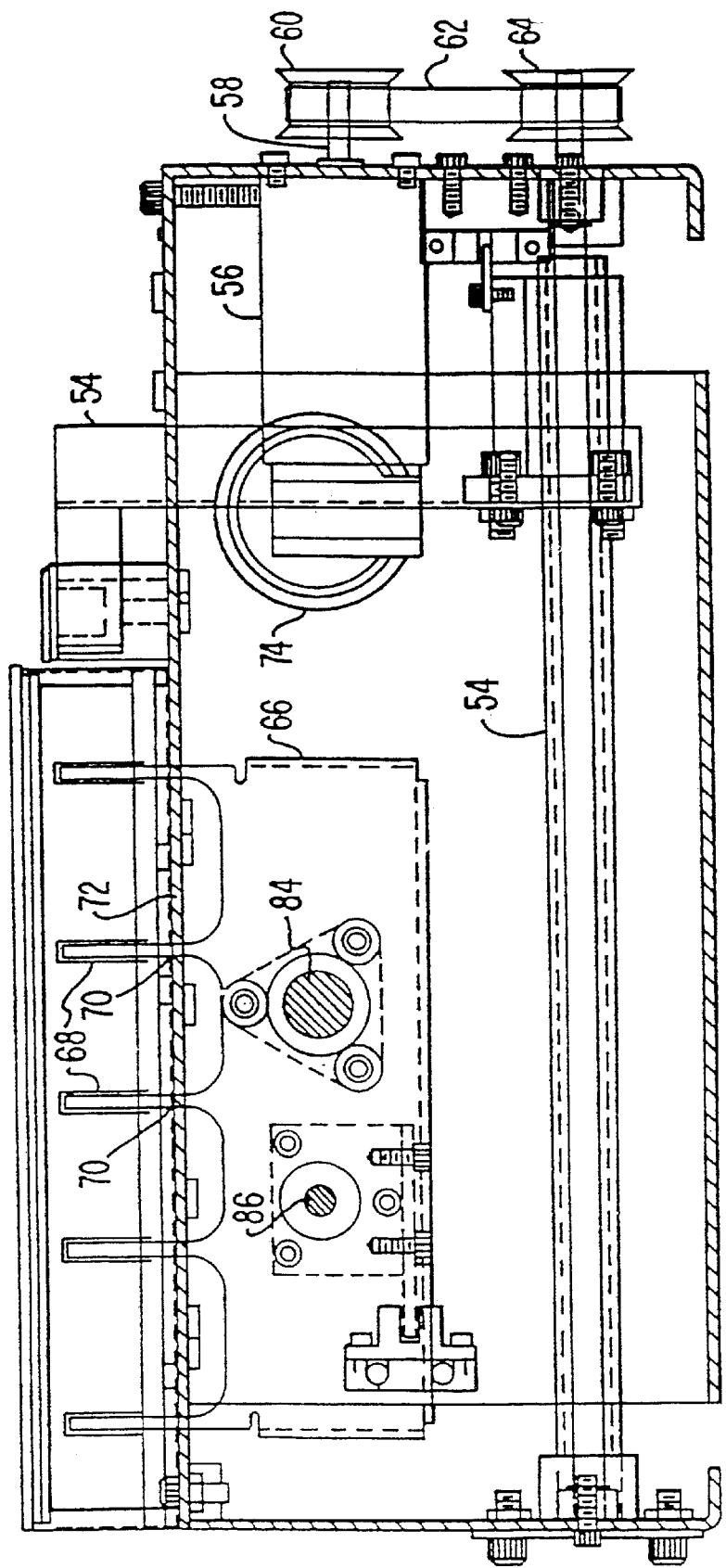
FIG. 18 is a schematic right-side elevation of the cuvette storage device of FIG. 15.
Figure 19:
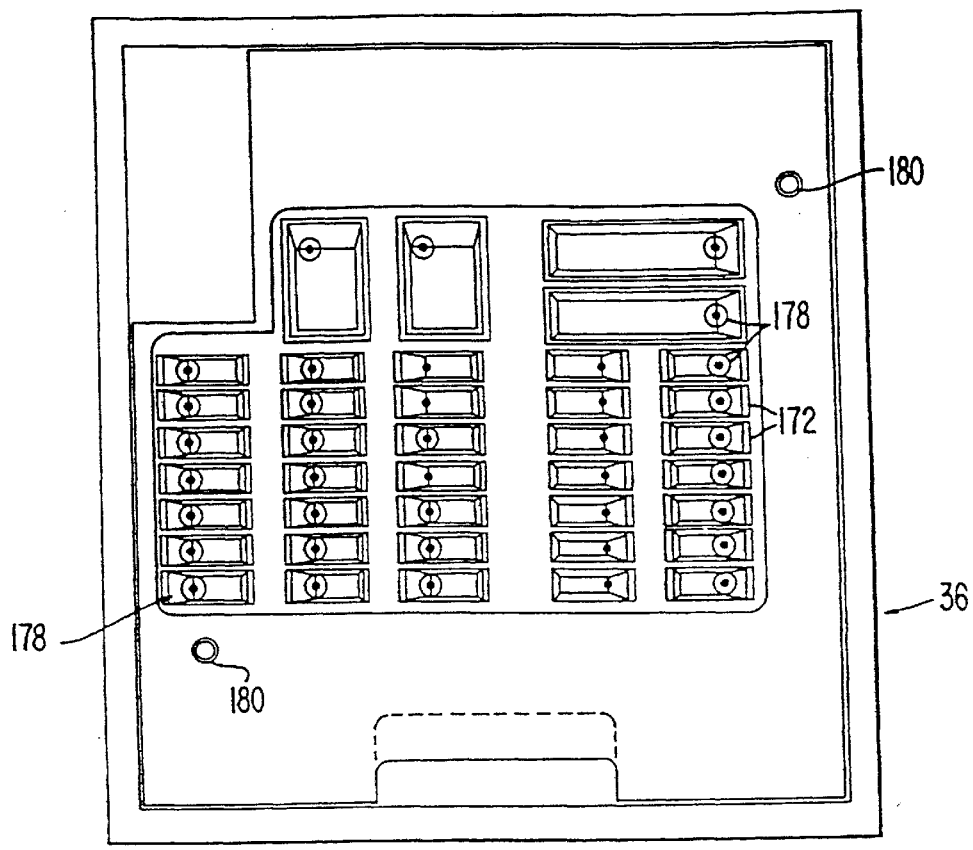
FIG. 19 is a top elevation of the reagent container block of FIG. 15.
Figure 20:
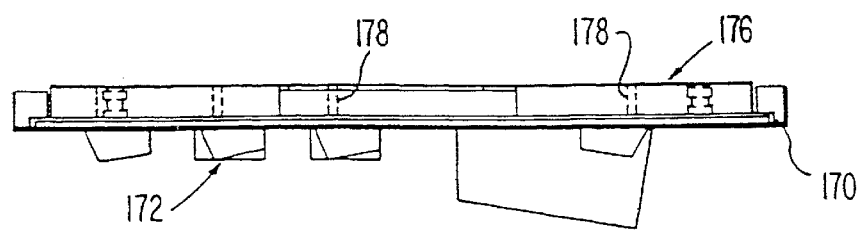
FIG. 20 is a side elevation of FIG. 19.

The heme unit of the hemoglobin molecule has adsorption at the 535nm band pass (see FIG. 15).

Bilirubin is conducted the same way but uses 450 nm and 710 nm as the wavelengths of interest, while lipemia is measured by monitoring the normalized transmittance at 710 nm.

II. Sample Preparation

The next step is the automatic preparation of the sample for testing. This includes the ability of the analyzer to access any reagent and to deposit it in a cuvette well; to wash the probe through which the reagent is accessed after each reagent is dispensed with a wash solution as described above in order to avoid cross-contamination problems between reagents or reagents and samples; a universal profile testing method for all coagulation assays; a means for automatically diluting the sample; and a means for monitoring levels of the reagents and samples in their cuvettes and tubes.

The random access movement of the probes is used to aspirate and dispense reagents and samples according to test protocol for a particular assay (defined by the adf parameters), ordered or scheduled from the bar code of a given sample collection tube. This movement, and a description of the analyzers instrumentation, is more fully explained in the U.S. Pat. No. 5,236,666. Correct reagent/plasma volume delivery is monitored through the use of a novel dye tracking system, one type of which is described in U.S. Pat. No. 5,068,181. The versatility provided by the presence of adf's allow the fully automated analyzer to be optimized for each specific assay, allowing for the flexibility required for radically different assay formats.

III. Optical Inspection

Once the reagents are added to the test sample, the reaction, if any, is read through spectrophotometric means. The optical inspection segment of the analyzer consists of a means for multiple wavelength analysis; a means to continuously normalize the fluctuations in light levels associated with sample to sample variability; and a means for using a broad spectrum of wavelengths in order to read the results of a variety of test reactions at the appropriate wavelength for that test.

The quality control programming insures proper wavelength selection by monitoring the signal noise to ratio for each sample as defined in the adf. If the signal to noise threshold is exceeded then another wavelength is used. If all wavelengths are unacceptable then an error flag is provided to the user.

The quality assurance programming assures that the true wavelength is being evaluated by incorporating a piece of spectral glass with known absorbance characteristics. The peaks are measured by the analyzer and compared to the known values. Furthermore, a liquid crystal clot simulator has been incorporated into the optics module that when properly stimulated creates a signal that is similar to a clot. The output is inspected to insure the integrity of the optics unit as well as the integrity of the analysis algorithms.

The operation of the sample handling system will now be described in the context of the following specific implementations of the invention, it being understood that the invention is not limited to these particular implementation.

Operation of the sample handling system according to the invention is centered on a linear track along which cuvettes are advanced from station to station by a lead screw. The basic timing and sequencing of the system is based on advancing the cuvettes along the linear track a distance equal to the distance between successive reaction wells.

Initially, an operator loads cuvettes into the instrument by placing a cassette of cuvettes into a cassette frame. Each cassette holds, for example, 120 cuvettes. The cuvettes are automatically moved from the cassette onto a loading ramp, thus allowing for uninterrupted flow of cuvettes while a cassette is being added to the system. Cuvettes are loaded from the ramp onto the linear track as scheduled, by an arm where they engage the lead screw. Each cuvette preferably has four ¼ inch reaction wells. The lead screw is activated every twenty seconds to move the cuvettes in 0.25 inch increments in 0.2 seconds. The instrument controller monitors each cuvette by the timing associated with the lead screw. The lead screw advances the cuvettes to the first station, i.e., the sample insertion station, where a sample is delivered to a reaction well aligned with the sample probe. After delivering the sample, the probe is automatically washed. Two minutes and 40 seconds later, the reaction well of the cuvette arrives at the first reagent delivery probe where diluent or a reagent is added, depending on the test being carried out. The probe is automatically washed after each delivery with a washing agent that is correct for removing that particular reagent. The second reagent probe is located two minutes and forty seconds after the first reagent probe, where an activator can be added. Three minutes and forty seconds later the loaded reaction well of the cuvette reaches the third reagent probe where a reagent is added and the reaction monitoring begins. The reaction is monitored electro-optically by an optical monitoring system, which measures changes in the optical transmission of the reaction volume as the clot forms or as the chromometric reaction proceeds. As the cuvette is moved along the track, the optical monitoring continues for twenty consecutive stations, that is, for 300 seconds. Following the optical monitoring station the cuvette leaves the track and is sent to a waste container.

Patient plasma samples are stored in a refrigerated housing in the original evacuated blood collection tubes used to obtain the patient's sample which has been previously spun down to obtain the plasma and bar coded for patient identification and test protocol to be performed. The evacuated sample collection tubes are placed in the holders of shuttles and advanced by the shuttle drive mechanism to the bar code reader. The evacuated sample collection tubes can be arranged in any order since the bar code on each sample collection tube allows the instrument to automatically correlate a patient with a given sample. The bar code read by bar code reader also programs the instrument controller for determining the amount of sample to be aspirated by the sample probe, the number of reaction wells to be filled with the sample, and the amounts and types of reagents/ buffers/ additives/activators to be injected into the respective reaction wells by multiple reagent probes. Subsequent to the programming station, a sample collection tube is advanced to a piercer where the piercing tube is caused to pierce the septum of the evacuated sample tube to allow the sample probe to be lowered into the sample collection tube to aspirate a programmed amount of sample. The sample probe is next removed from the evacuated sample collection tube and horizontally moved over a reaction well positioned at the sample insertion station and lowered into the reaction well where a programmed amount of sample is expelled into the reaction well. The evacuated sample collection tubes can be removed from the refrigerated housing at any time after sample aspiration is complete; however, because the samples are maintained at lowered temperatures, they can be retained for further testing without having to be immediately removed from its shuttle. The reagent chamber stores various controls, diluents, activators and reagents. In one implementation of the system up to twenty-two containers of these materials are stored in the reagent chamber. All containers are held to a temperature of about 9–15° C. and the reagents are heated, if necessary, in the reagent probe as they are being dispensed.

Pumping in all cases is performed with positive displacement syringe pumps operatively connected with respective ones of the probe. No manipulation of pump tubing is required as is the case with peristaltic pumps. A reagent is dispensed into a reaction well in a manner that promotes mixing with the sample and other contents of the reaction well. The reagent temperature and volume are controlled by the instrument controller.

Desirably, fluid level sensing is utilized to control the height of a reagent probe relative to the level of a reagent in its container and relative to the contents of a reaction well. This permits bringing the outside of a probe into contact with a minimum quantity of reagent. This, in turn, reduces the possibility for carry-over. Additionally, level sensing is used to control the height of a probe above the fluid level while dispensing in order to minimize carry-over and to maximize mixing.

At the same time that all of the above mechanical and programmed functions are occurring, various quality assurance/quality control checks are being automatically performed. Also, data calculations are being automatically performed in order to produce and deliver a final result of the parameter being assayed for.

It is to be understood that the invention described and illustrated herein is to be taken as a preferred example of the same, and that various changes in the method and apparatus of the invention may be resorted to, without departing from the spirit of the invention or scope of the claims

We claim:

1. An apparatus for performing at least one time-dependent measurement on an unknown sample to derive at least one time-dependent measurement profile, and predicting the presence of at least one congenital or acquired imbalance or therapeutic condition associated with thrombosis/hemostasis from the at least one time-dependent measurement profile, comprising:
    a) means for performing at least one time-dependent measurement on said unknown sample of a property over time, which property changes when said unknown sample undergoes coagulation, so as to derive at least one time-dependent measurement profile;
    b) means for defining a set of a plurality of predictor variables which sufficiently define the data of the at least one time-dependent measurement profile;
    c) means for deriving a model that represents the relationship between the at least one congenital or acquired imbalance or therapeutic condition, and the set of a plurality of predictor variables; and
    d) means for utilizing the model of step c) to predict the existence of the at least one congenital or acquired imbalance or therapeutic condition in the unknown sample.

2. An apparatus according to claim 1, wherein said means for performing at least one time-dependent measurement comprises an optical system for performing at least one optical measurement of said unknown sample over time and so as to derive an at least one optical profile.

3. An apparatus according to claim 2, wherein said optical system is part of an automated analyzer for thrombosis and hemostasis testing.

4. An apparatus according to claim 3 which is an automated analyzer for thrombosis and hemostasis testing, and wherein said at least one optical profile is provided automatically by said automated analyzer, wherein said unknown sample is automatically removed by an automated probe from a sample container to a test well, one or more reagents are automatically added to said test well so as to initiate said changes of a property within said unknown sample, and the development of said changes of said property over time is automatically optically monitored so as to derive said at least one optical profile.

5. An apparatus according to claim 4, further comprising at least one of a memory and a display wherein a predicted congenital or acquired imbalance or therapeutic condition is automatically stored in said memory and/or displayed on said display.

6. An apparatus according to claim 4, further comprising means for automatically performing one or more assays for confirming the existence of said at least one congenital or acquired imbalance or therapeutic condition.

7. An apparatus according to claim 6, wherein said means for automatically performing one or more confirming assays is an automatic performing means wherein said one or more confirming assays are automatically ordered and performed on said automated analyzer, with results of said one or more confirming assays being stored in a memory of said automated analyzer and/or displayed on a display of said automated analyzer.

8. An apparatus according to claim 2, wherein said optical system comprises a system for performing a plurality of optical measurements at one or more wavelengths over time so as to derive said at least one optical profile, said plurality of optical measurements corresponding to changes in light scattering and/or light absorption in the unknown sample.

9. An apparatus according to claim 2, wherein in said optical system, a plurality of optical measurements are taken over time so as to derive said at least one optical profile, and wherein said plurality of optical measurements are each normalized to a first optical measurement.

10. An apparatus according to claim 1, further comprising means for providing a set of data from known samples, which set of data is used in said means for deriving a model.

11. An apparatus according to claim 10, wherein said set of data from known samples is provided by a means for performing a plurality of assays on said known samples.

12. An apparatus according to claim 10, wherein said means for deriving a model is a means for deriving a model by means of a neural network.

13. An apparatus according to claim 1, wherein said relationship determined by said deriving means is determined via at least one automated algorithm.

14. An apparatus according to claim 13, wherein said model is a multilayer perceptron, and wherein said at least one automatic algorithm is a back propagation learning algorithm.

15. An apparatus according to claim 1, wherein said means for performing at least one time-dependent measurement will perform a purality of time-dependent measurement profiles.

16. An apparatus according to claim 1, wherein said means for performing a purality of time-dependent measurement profiles includes a means for performing at least two profiles from assays initiated with PT (prothrombin time) reagents, APPT (activated partial thrombin time) reagents, fibrinogen reagents and TT (thrombin time) reagents.

17. An apparatus according to claim 1, wherein said set of predictor variables includes one or more of: a minimum of the first derivative of the at least one time-dependent profile, a time index of the minimum of the first derivative, a minimum of the second derivative of the at least one time-dependent profile, a time index of the minimum of the second derivative, a maximum of the second derivative of the profile, a time index of the maximum of the second derivative, an overall change in the coagulation parameter during the time- dependent measurement on the unknown sample, a clotting time, a slope of the profile prior to clot formation, and a slope of the profile after clot formation.

18. An apparatus according to claim 17, wherein three or more predictor variables are within said set of data.

19. An apparatus according to claim 18, wherein more than three predictor variables are within said set of data.

20. An apparatus according to claim 1, wherein said unknown sample is a sample from a medical patient, and wherein said utilizing means comprises a means for utilizing both said model and additional patient medical data for predicting the existence of said at least one congenital or acquired imbalance or therapeutic condition.

21. An automated analyzer for predicting the presence of at least one congenital or acquired imbalance or therapeutic condition associated with thrombosis or hemostasis from at least one time-dependent measurement profile, comprising:
- a specimen handling station comprising a sample container having therein a sample to be tested;
- a test well;
- an automated probe for removing the sample from the sample container and adding the sample to the test well;
- a reagent station having one or more reagents to be combined with said sample in said test well so as to cause coagulation in said sample;
- an inspection station for monitoring the development of a property of said sample over time after combination with at least one reagent, which property changes when said sample undergoes coagulation, so as to derive a respective at least one time-dependent measurement profile;
- a processor for a) defining a set of a plurality of predictor variables which define the at least one time-dependent measurement profile, b) deriving a model that represents the relationship between the at least one congenital or acquired imbalance or therapeutic condition associated with thrombosis or hemostasis, and the set of a plurality of predictor variables, and c) utilizing the model to predict the presence of the at least one congenital or acquired imbalance or therapeutic condition associated with thrombosis or hemostasis in the sample.

22. The automated analyzer of claim 21, wherein said inspection station comprises an optical system for performing at least one optical measurement over time so as to derive the respective at least one time-dependent measurement profile.

23. The automated analyzer according to claim 22, wherein said optical system comprises a light source for passing light through said test well and a light detector for detecting light passed through or scattered by said test well.

24. The automated analyzer according to claim 23, wherein said light detector will detect light at regular time intervals.

25. The automated analyzer according to claim 23, wherein said light detector will detect multiple wavelengths.

26. The automated analyzer according to claim 21, further comprising a memory or a display or both, where a predicted at least one congenital or acquired imbalance or therapeutic condition is automatically stored in said memory and/or displayed on said display.

27. The automated analyzer according to claim 21, further comprising a memory device for storing data from known samples for use in said processor for deriving said model.

28. The automated analyzer according to claim 21, wherein alternatives for or additions to the set of a purality of predictor variables include coefficients of a curve fitted to a data profile, pattern recognition, and clot time-based parameters.

29. The automated analyzer according to claim 21, wherein said test well is within a cuvette which has a plurality of test wells.

30. The automated analyzer according to claim 21, wherein said test well is within a cuvette having a bar code thereon, and said automated analyzer comprises a patient identification and tracking device which utilizes said bar code.

31. The automated analyzer according to claim 20, further comprising an assay definition file that allows for flexibility in how reagents and plasmas are delivered.

32. The automated analyzer according to claim 21, further comprising one or more movable probes for aspirating reagents from said reagent station and adding to said test well.

33. The automated analyzer according to claim 21, wherein said sample container is an evacuated collection tube with a pierceable stopper.

34. The automated analyzer according to claim 21, wherein said model that represents the relationship is determined via at least one automated algorithm.

35. The automated analyzer according to claim 34, wherein said model is a multilayer perceptron, and wherein said at least one automated algorithm is a back propagation learning algorithm.

* * * * *